(12) United States Patent
Foerster

(10) Patent No.: US 8,337,602 B2
(45) Date of Patent: Dec. 25, 2012

(54) DEODORIZING DEVICE AND KIT, AND METHODS FOR ODOR REMOVAL

(75) Inventor: Lee Foerster, Medford, OR (US)

(73) Assignee: TF Industries, LLC, Medford, OR (US)

( * ) Notice: Subject to any disclaimer, the term of this patent is extended or adjusted under 35 U.S.C. 154(b) by 506 days.

(21) Appl. No.: 12/579,875

(22) Filed: Oct. 15, 2009

(65) Prior Publication Data

US 2010/0089235 A1   Apr. 15, 2010

Related U.S. Application Data

(60) Provisional application No. 61/140,395, filed on Dec. 23, 2008, provisional application No. 61/105,501, filed on Oct. 15, 2008.

(51) Int. Cl.
*B01D 53/02* (2006.01)

(52) U.S. Cl. ............. 96/147; 96/108; 55/385.1; 55/467; 55/471

(58) Field of Classification Search ............. 95/90, 273; 96/108, 147; 55/385.1, 467, 471
See application file for complete search history.

(56) References Cited

U.S. PATENT DOCUMENTS

| | | |
|---|---|---|
| 1,798,457 A | 3/1931 | Cole |
| 2,009,054 A | 7/1935 | Mooney |
| 2,214,200 A | 9/1940 | Lowther |
| 2,747,201 A | 5/1956 | Herriott |
| 2,846,696 A | 8/1958 | Herriott |
| 2,990,557 A | 7/1961 | Witherell |
| 3,192,539 A | 7/1965 | Martz |
| 3,287,743 A | 11/1966 | Coates |
| 3,585,651 A | 6/1971 | Cox |
| 3,649,972 A | 3/1972 | Sowards |
| 3,733,619 A | 5/1973 | Smith |
| 3,781,923 A | 1/1974 | Maisch |
| 3,857,119 A | 12/1974 | Hunnicutt, Jr. |
| 4,059,857 A | 11/1977 | Poister |
| 4,099,047 A | 7/1978 | Kirkland, Jr. |
| 4,200,940 A | 5/1980 | Buchanan |
| 4,317,242 A | 3/1982 | Stamper |
| 4,375,704 A | 3/1983 | Smith |
| 4,472,841 A | 9/1984 | Faulkner |
| 4,493,117 A | 1/1985 | Sguazzin |
| 4,541,847 A * | 9/1985 | Oie et al. ............ 96/58 |
| 4,693,337 A | 9/1987 | Timmermeister |
| 4,701,966 A | 10/1987 | Schafer |
| 4,876,748 A | 10/1989 | Chun |
| 5,161,262 A | 11/1992 | Quaintance, Sr. |

(Continued)

OTHER PUBLICATIONS

International Search Report and Written Opinion, PCT/US09/60812, 2009.

(Continued)

*Primary Examiner* — Duane Smith
*Assistant Examiner* — Christopher P Jones
(74) *Attorney, Agent, or Firm* — Berenato & White, LLC

(57) ABSTRACT

A deodorizing device is provided featuring a collection mouthpiece having an intake port and an internal channel, and a pump unit attachable to the collection mouthpiece and operable to draw malodorous air into the intake port and through the internal channel when the collection mouthpiece is attached to the pump unit. Also provided are a pump unit, a filter cartridge, a mount, and methods of assembling and using the same.

20 Claims, 17 Drawing Sheets

U.S. PATENT DOCUMENTS

| | | | |
|---|---|---|---|
| 5,231,705 A | | 8/1993 | Ragusa |
| 5,253,371 A | | 10/1993 | Slawinski |
| 5,255,395 A | | 10/1993 | Millette |
| D349,338 S | | 8/1994 | Crinion |
| 5,369,812 A | | 12/1994 | Trombley |
| 5,386,594 A | | 2/1995 | Hilton |
| 5,452,481 A | | 9/1995 | Meyer |
| 5,454,122 A | * | 10/1995 | Bergeron .................. 4/217 |
| 5,530,971 A | | 7/1996 | Anderson |
| D377,390 S | | 1/1997 | Ketcham |
| D382,549 S | | 8/1997 | Yoshimoto |
| 5,704,074 A | | 1/1998 | Baldea |
| 5,781,937 A | | 7/1998 | Liang |
| 5,850,638 A | | 12/1998 | Her |
| 5,875,496 A | | 3/1999 | Schaffer |
| 5,948,398 A | | 9/1999 | Hanamoto et al. |
| 5,997,674 A | | 12/1999 | Rakocy et al. |
| 6,041,449 A | | 3/2000 | Brown et al. |
| 6,186,140 B1 | * | 2/2001 | Hoague ................. 128/202.22 |
| 6,209,146 B1 | | 4/2001 | Gonzalez |
| 6,233,750 B1 | | 5/2001 | Donald et al. |
| D444,218 S | | 6/2001 | Mittelstadt et al. |
| 6,260,214 B1 | | 7/2001 | Smith |
| D452,302 S | | 12/2001 | Hagen |
| 6,344,065 B1 | | 2/2002 | Boulva |
| D455,826 S | | 4/2002 | Gillingham et al. |
| 6,363,542 B1 | | 4/2002 | Pope, Sr. |
| 6,523,184 B2 | | 2/2003 | Prisco |
| 6,550,072 B1 | | 4/2003 | Ware |
| 6,584,620 B1 | | 7/2003 | Reutov et al. |
| 6,589,323 B1 | * | 7/2003 | Korin ............................ 96/223 |
| 6,610,121 B2 | * | 8/2003 | Chasen ............................ 95/1 |
| D480,127 S | | 9/2003 | Cox et al. |
| 6,615,410 B1 | | 9/2003 | Gurrola |
| 6,643,850 B2 | | 11/2003 | Chasen et al. |
| 6,660,060 B2 | * | 12/2003 | Chasen ............................ 95/1 |
| 6,678,900 B2 | | 1/2004 | Ware |
| 6,795,980 B1 | | 9/2004 | Ries |
| 6,946,021 B2 | * | 9/2005 | Aoyagi ........................ 96/226 |
| D511,377 S | | 11/2005 | Erwan et al. |
| D558,870 S | | 1/2008 | Triplett et al. |
| D588,257 S | | 3/2009 | Reedy et al. |
| D598,088 S | | 8/2009 | Foerster |
| 2007/0240250 A1 | * | 10/2007 | Foerster et al. .................. 4/213 |

OTHER PUBLICATIONS

Hepalta Purified Air Inc., http://www.hepalta.com/ambifresh, Printed Apr. 17, 2006.
OdorVac, http://www.odorvac.com/, Printed Apr. 17, 2006.
Miracle Seat, http://www.miracleseat.com/, 2003.
http://www.panfan.com/ (3 pages).
http://www.hamiltonbeach.com/special-lines-trueair.html (2 pages), 2009.
http://www.businessedge.ca/article.cfm/newsID/4176.cfm (2 pages), 2003.
http://www.brondell.com/products/Breezaintro.php (2 pages).

\* cited by examiner

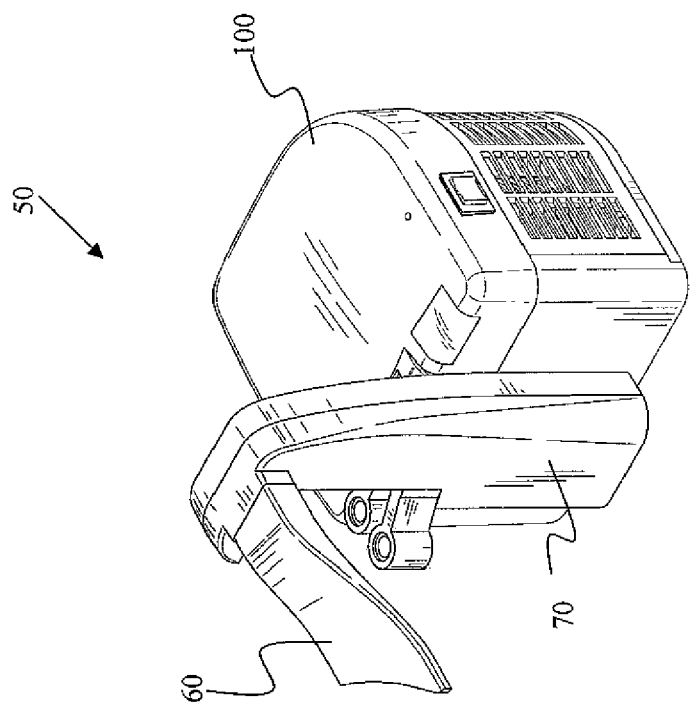
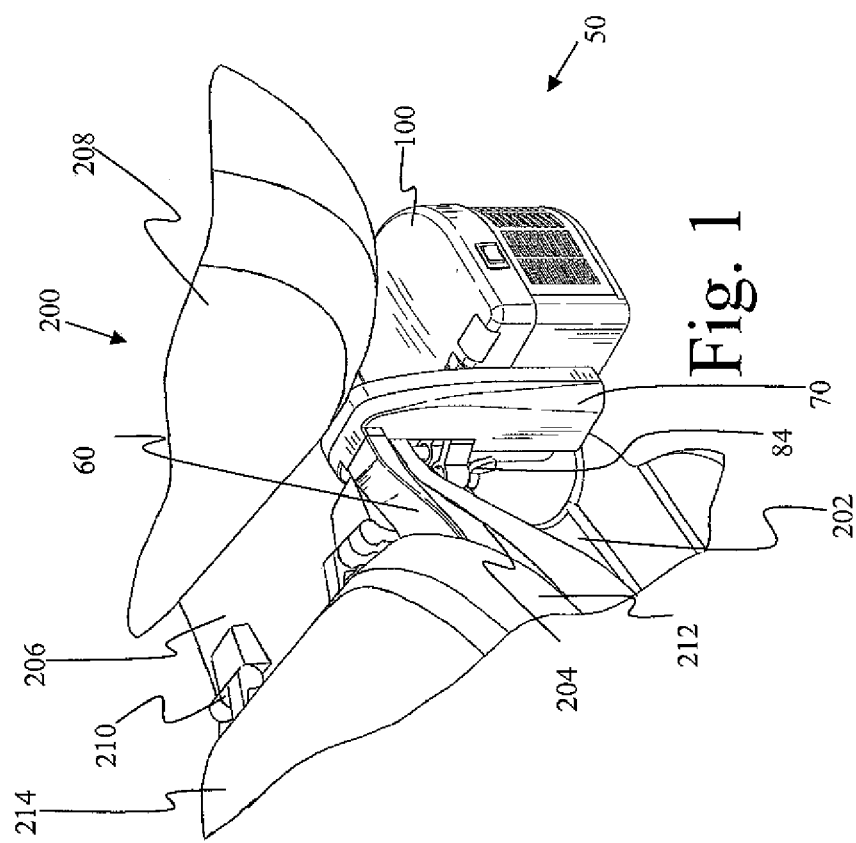

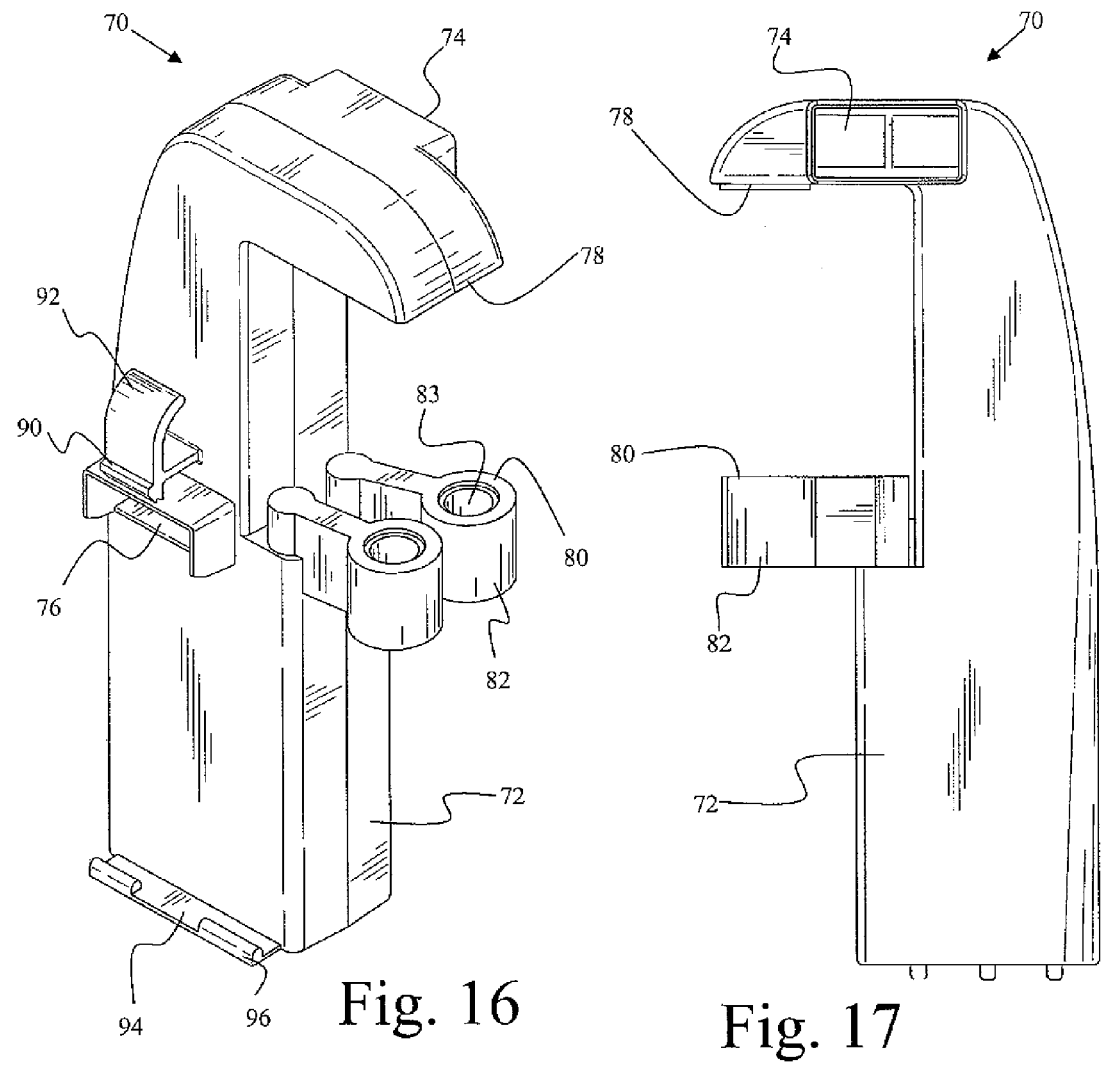

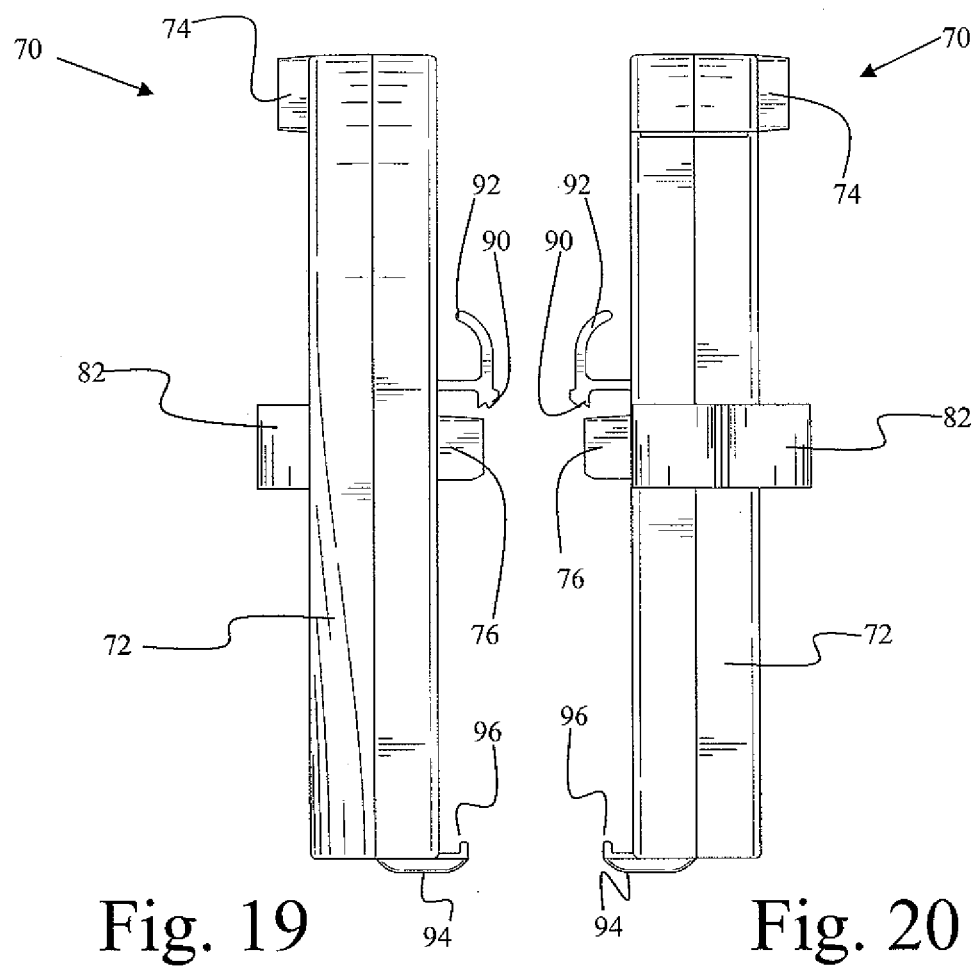
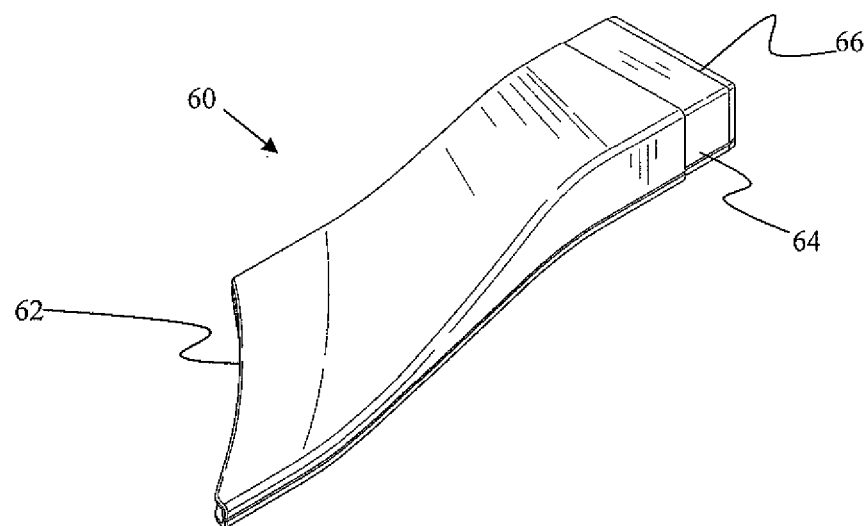

DEODORIZING DEVICE AND KIT, AND METHODS FOR ODOR REMOVAL

CROSS-REFERENCE TO RELATED APPLICATIONS

This application claims the benefit of priority of U.S. provisional applications 61/140,395 filed Dec. 23, 2008 and 61/105,501 filed Oct. 15, 2008, the complete disclosures of which are incorporated herein by reference.

FIELD OF THE INVENTION

The present invention generally relates to a deodorizing device, and in particularly exemplary embodiments to a universal deodorizing device useful as a toilet odor removal system designed to simplify maintenance and cleaning of a toilet bowl. The present invention also relates to a kit for making the deodorizing device, and methods of making and using the kit and the deodorizing device, including retrofitting.

BACKGROUND OF THE INVENTION

Numerous devices have been proposed for the removal or neutralization of objectionable, obnoxious odors generated from defecation in toilets. While such devices are generally intended for improving sanitation and air quality by permitting the withdrawal of malodorous fumes for treatment or for expulsion to an outside environment, the devices suffer from drawbacks. For example, known ventilation devices are cumbersome, and typically contain unsightly vent hoses or pipes that make them aesthetically unacceptable to discerning consumers. Further, installation of ventilation devices frequently requires expensive and permanent modifications to the bathroom structural interiors and/or to the toilet itself.

Conventional filtration and deodorizing devices are designed to eliminate odors and then exhaust purified air back into the bathroom. In theory, such devices negate the need for extensive installation procedures, lengthy vent hoses or pipes, and costly toilet and room modifications. However, these systems generally do not thoroughly neutralize obnoxious odors. Systems that recirculate air through a filter in multiple passes may be more effective in neutralizing odors, but do so at the cost of higher energy consumption, which can be particularly problematic when the device is battery powered and therefore has a finite energy capacity. Other devices add fragrance to processed air to mask odors. The scents of such fragrances are not always effective in their masking, and are not acceptable to many consumers. As a consequence, conventional deodorizing devices have not been accepted on a broad range and have enjoyed limited commercial success.

SUMMARY OF THE INVENTION

According to a first aspect of this invention there is provided a deodorizing device featuring a collection mouthpiece having an intake port and an internal channel, and a pump unit attachable to the collection mouthpiece and operable to draw malodorous air into the intake port and through the internal channel when the collection mouthpiece is attached to the pump unit. The pump unit includes a replaceable filter cartridge and an internal compression chamber for receiving the malodorous air. The filter cartridge includes a housing and a filter material contained in the housing for treating the malodorous air. The filter cartridge housing includes first and second wall portions angled relative to one another and extending along respective sides of the pump unit. The first and second wall portions respectively have first and second exterior surface regions with flow openings for expelling the treated air from the pump unit and further respectively have first and second internal surface regions adjacent to the internal compression chamber for receiving the malodorous air for treatment.

A second aspect of the invention provides a deodorizing device featuring a pump unit including a motor and impeller operably associated with an inlet port for drawing malodorous air through the inlet port into an internal compression chamber in the pump unit. The pump unit further includes a filter material for receiving and treating the malodorous air. The filter material contains activated carbon granules having a particle size distribution that can pass through a mesh having a U.S. sieve size number (ASTM) of about 12.

A third aspect of the invention provides a method of operating a deodorizing device using a pump unit including a motor and impeller operably associated with an inlet port and an internal compression chamber of the pump unit. The pump unit further includes a restrictive-flow filter material downstream from the internal compression chamber. The impeller is operated to draw malodorous air through the inlet port and into the internal compression chamber at a first flow rate. Flow of the malodorous air is restricted through the filter material to a second flow rate that is less than the first flow rate, and simultaneously pressure build-up in the internal compression chamber is generated.

Other aspects of the invention include other combinations of components of the deodorizing device, individual components (e.g., the pump unit, mount, collection mouthpiece, filter cartridge housing, and filter material), kits for making the deodorizing device, and methods of making, assembling and using the deodorizing device and its components.

BRIEF DESCRIPTION OF THE DRAWINGS

The accompanying drawings are incorporated in and constitute a part of the specification. The drawings, together with the general description given above and the detailed description of the exemplary embodiments and methods given below, serve to explain the principles of the invention. In such drawings:

FIG. 1 is an upper perspective view of a deodorizing device mounted on a toilet according to an exemplary embodiment of the invention;

FIG. 2 is an upper perspective view of the deodorizing device of FIG. 1 in a non-mounted position;

FIG. 16 is an enlarged, upper perspective view of a mount of the deodorizing device of FIG. 1;

FIG. 17 is an enlarged front view of the mount of FIG. 16;

FIG. 19 is an enlarged right side view of the mount of FIG. 16;

FIG. 20 is an enlarged left side view of the mount of FIG. 16;

FIG. 23 is an enlarged, upper perspective view of a collection mouthpiece of the deodorizing device of FIG. 1;

Figure 3:
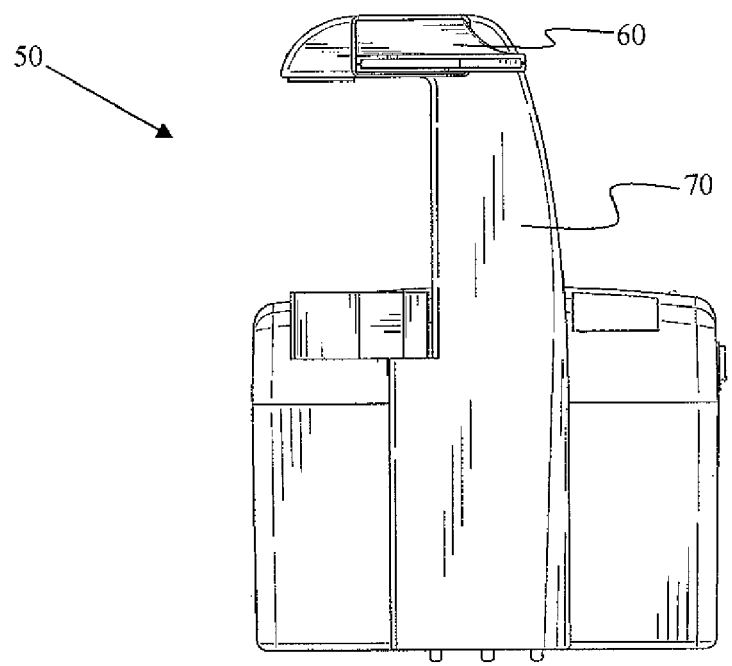
FIG. 3 is a front view of the deodorizing device of FIG. 1.
Figure 4:
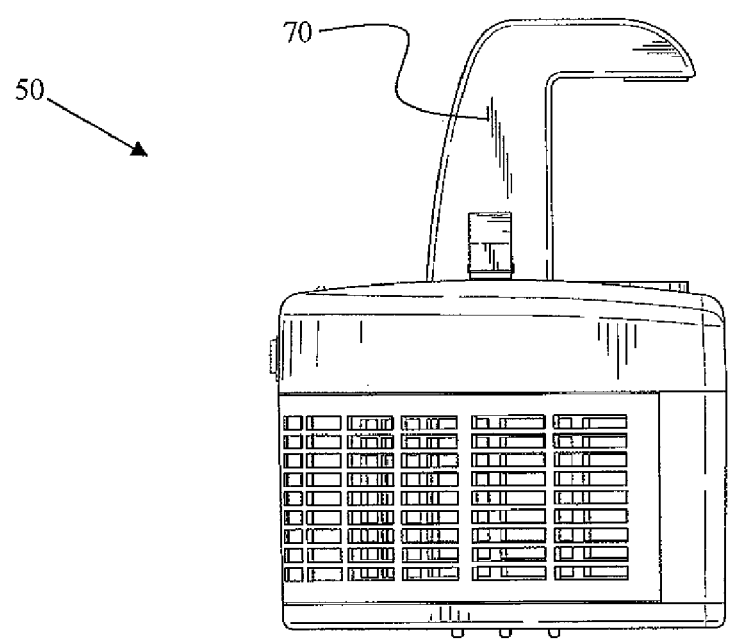
FIG. 4 is a rear view of the deodorizing device of FIG. 1.
Figure 6:
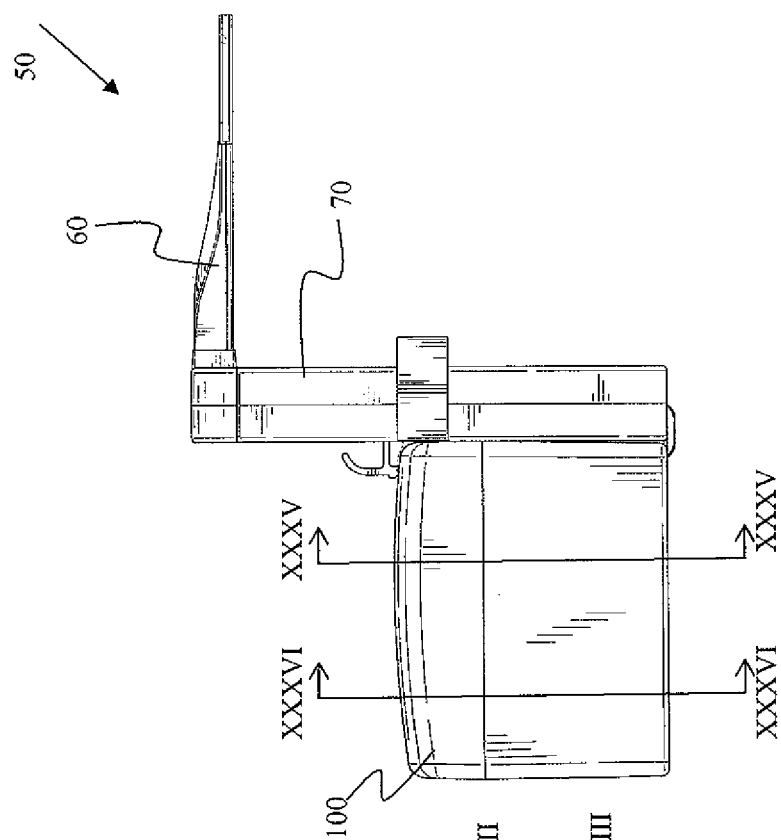
FIG. 6 is a left side view of the deodorizing device of FIG. 1.
Figure 5:
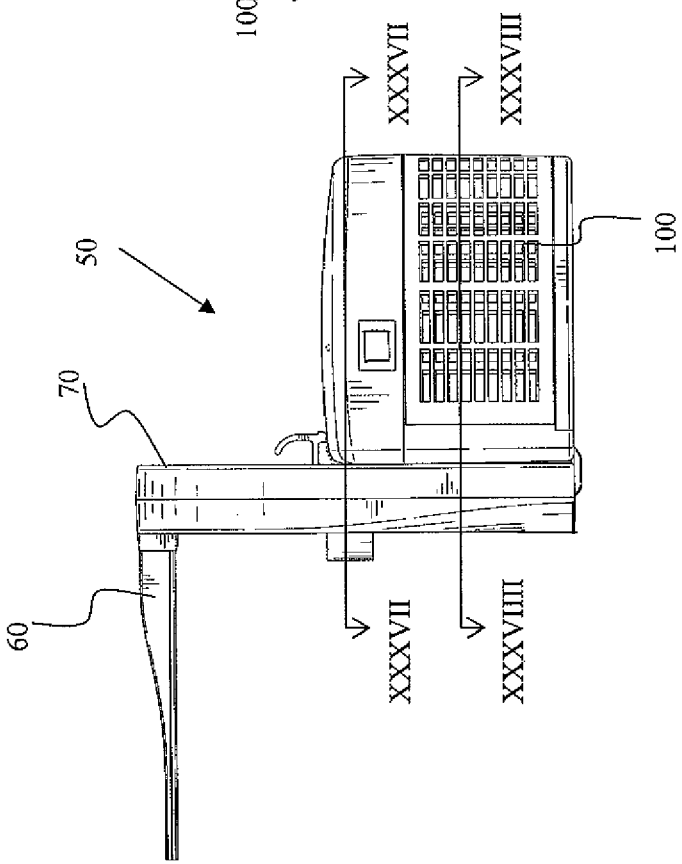
FIG. 5 is a right side view of the deodorizing device of FIG. 1.
Figure 7:
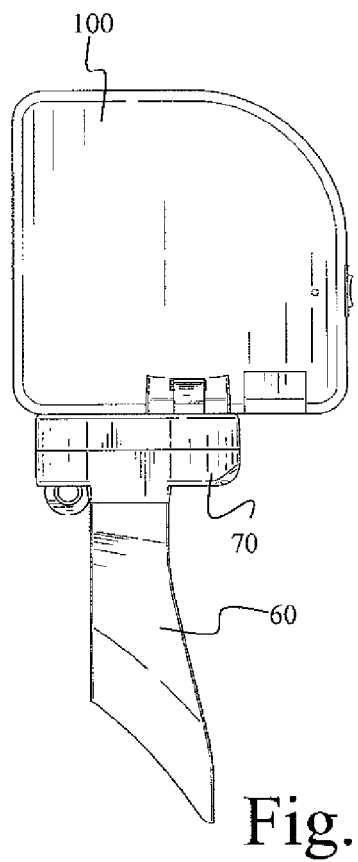
FIG. 7 is a top view of the deodorizing device of FIG. 1.
Figure 8:
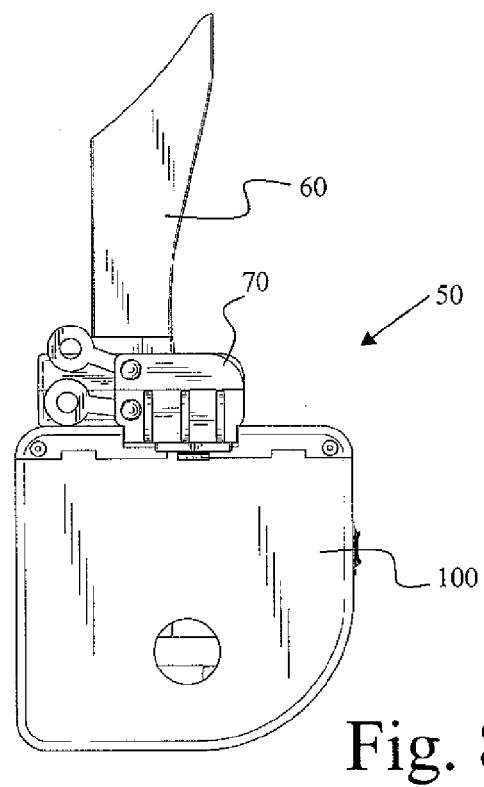
FIG. 8 is a bottom view of the deodorizing device of FIG. 1.
Figure 9:
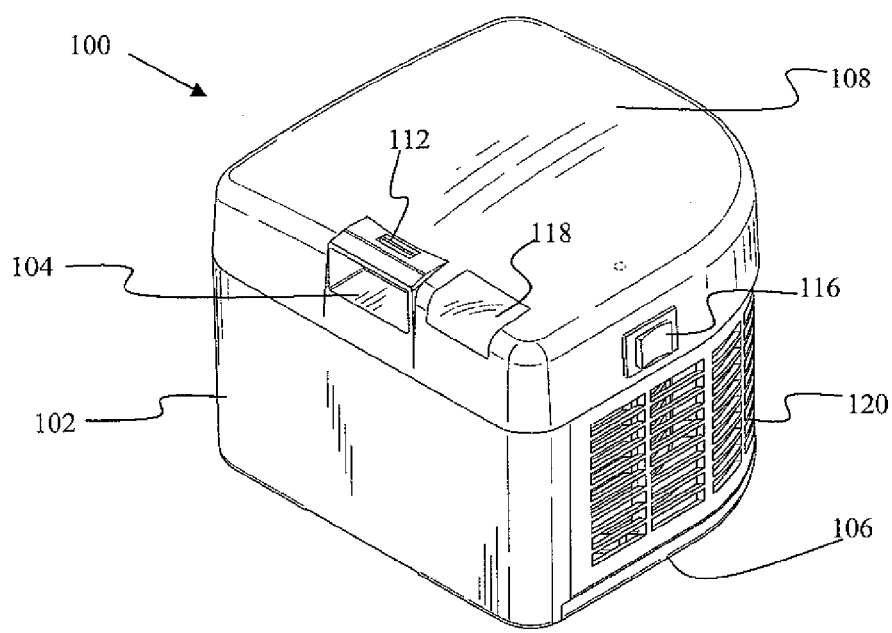
FIG. 9 is an enlarged, upper perspective view of a pump unit of the deodorizing device of FIG. 1.
Figure 10:
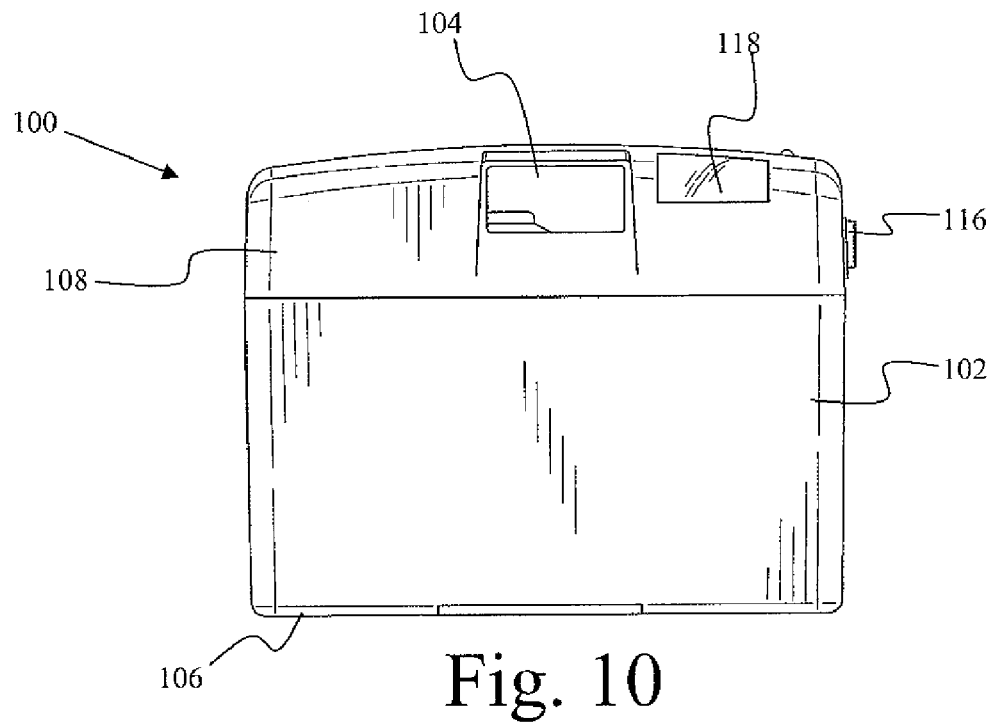
FIG. 10 is an enlarged front view of the pump unit of FIG. 9.
Figure 11:
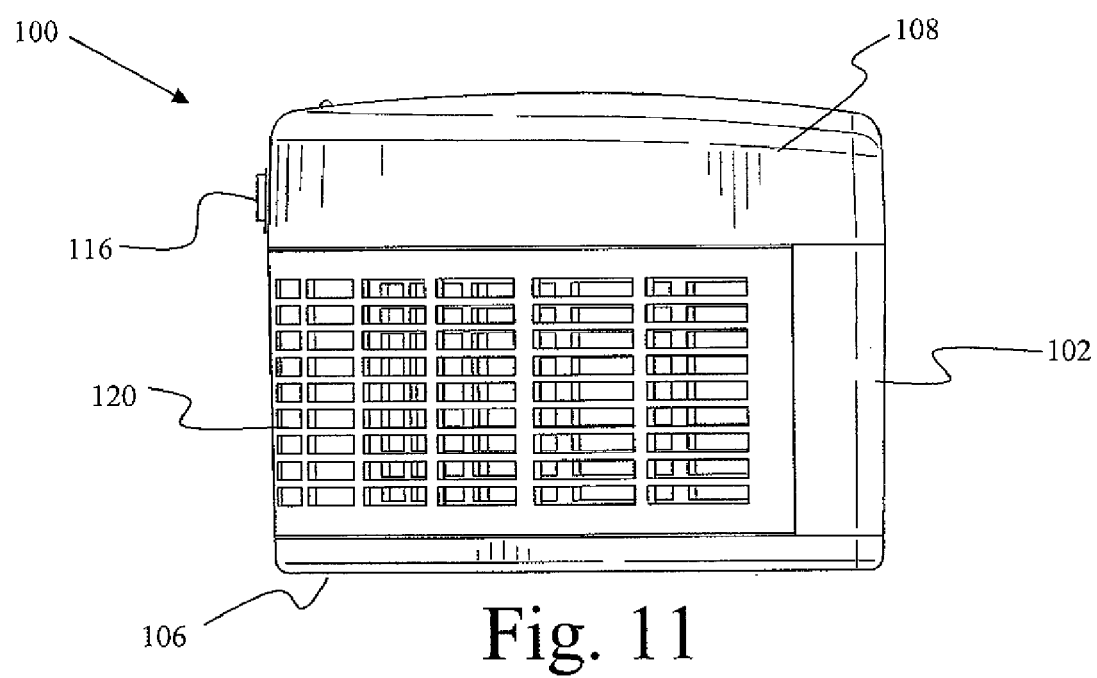
FIG. 11 is an enlarged rear view of the pump unit of FIG. 9.
Figure 12:
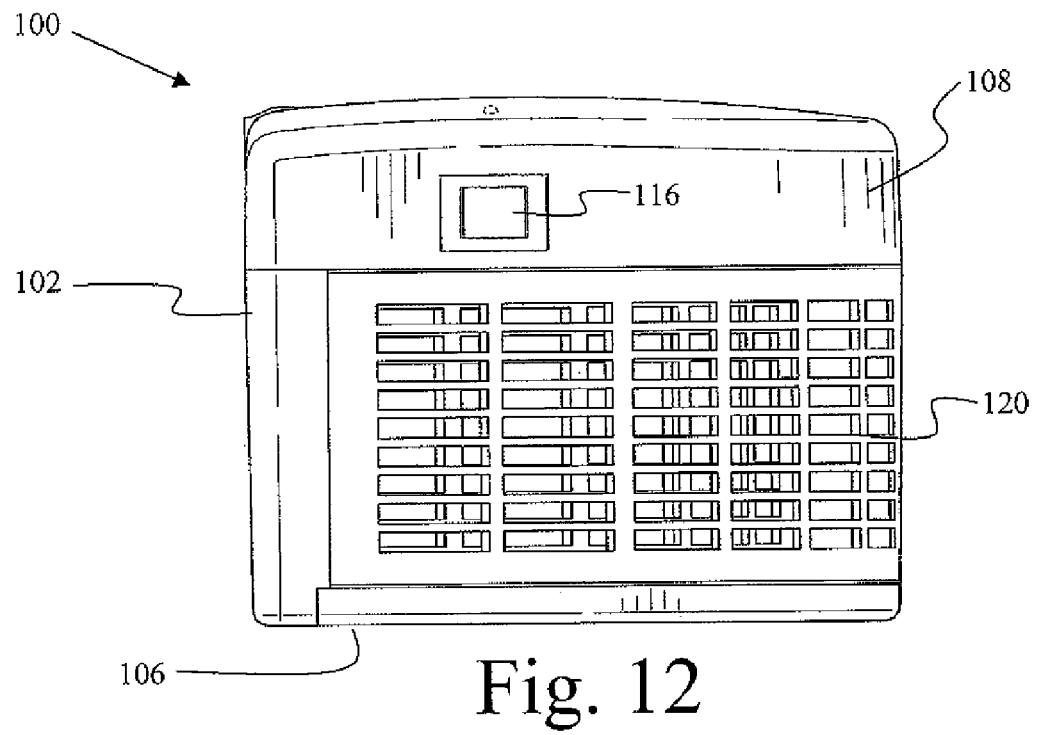
FIG. 12 is an enlarged right side view of the pump unit of FIG. 9.
Figure 13:
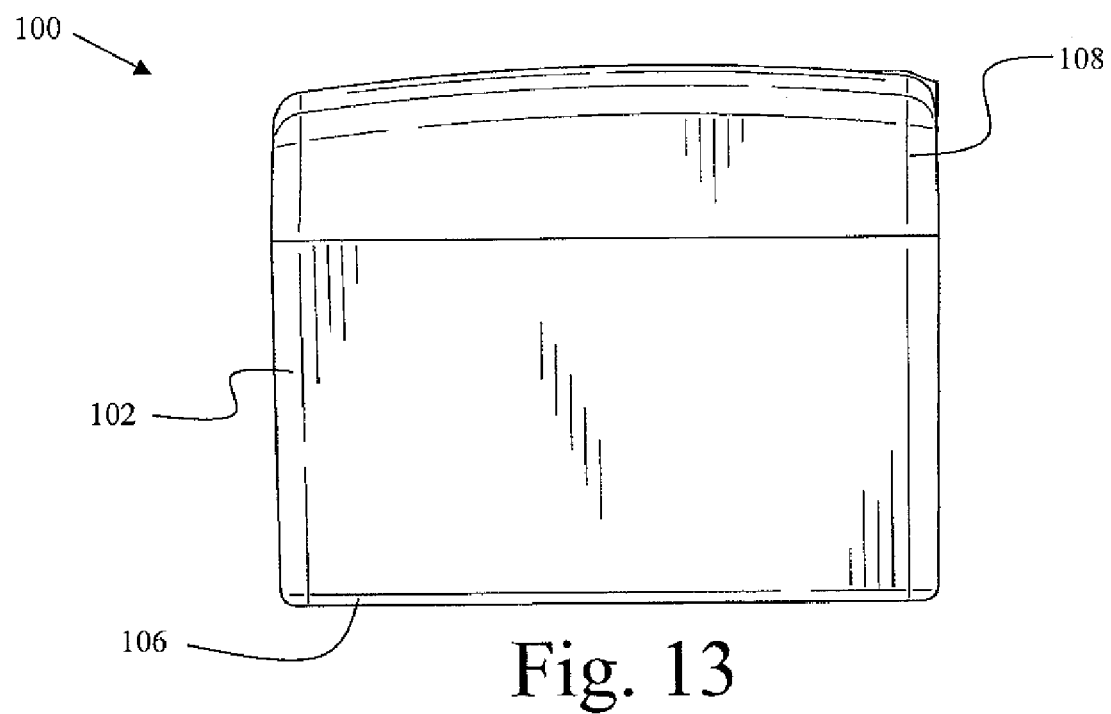
FIG. 13 is an enlarged left side view of the pump unit of FIG. 9.
Figure 14:
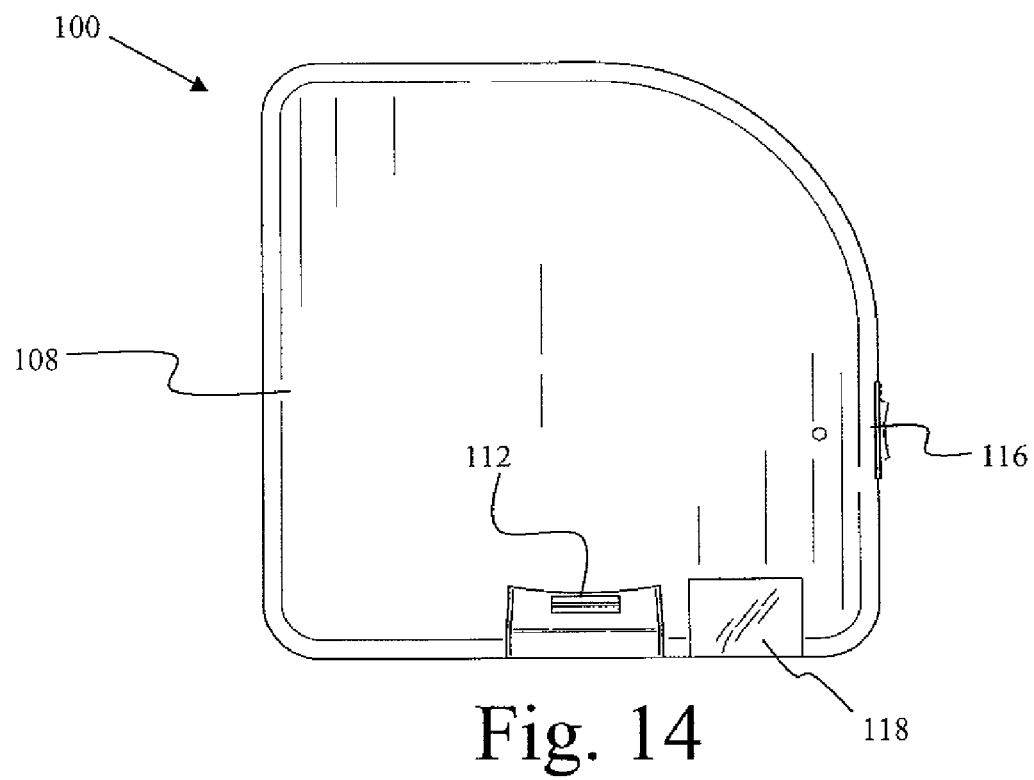
FIG. 14 is an enlarged top view of the pump unit of FIG. 9.
Figure 15:
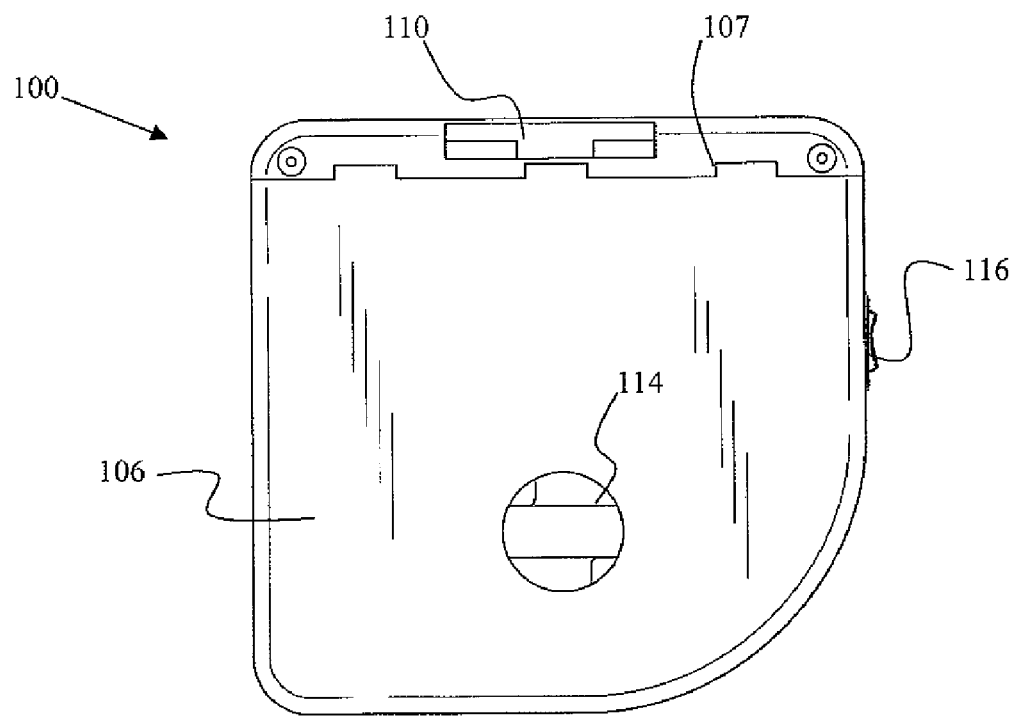
FIG. 15 is an enlarged bottom view of the pump unit of FIG. 9.
Figure 18:
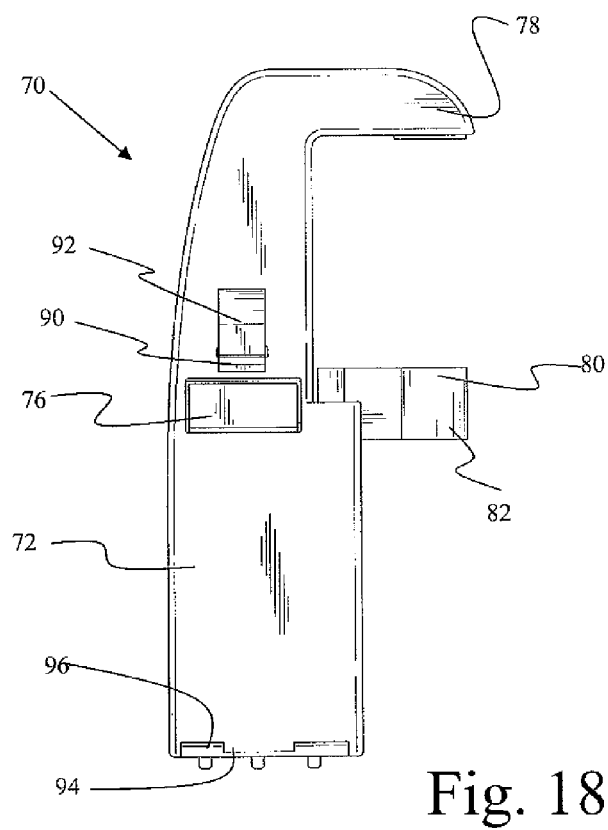
FIG. 18 is an enlarged rear view of the mount of FIG. 16.
Figure 21:
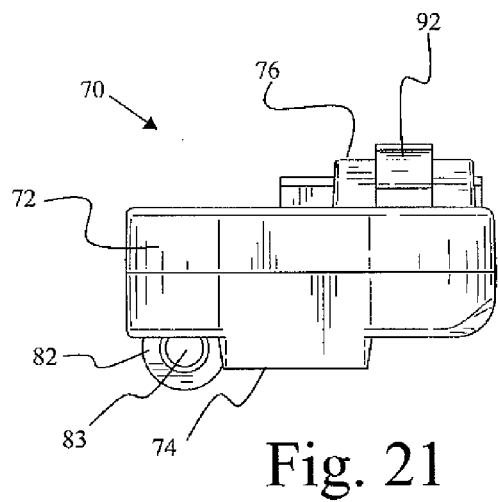
FIG. 21 is an enlarged top view of the mount of FIG. 16.
Figure 22:
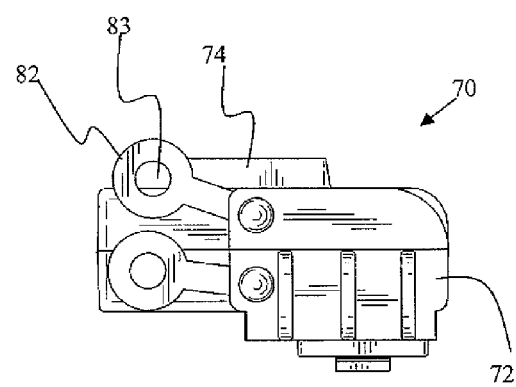
FIG. 22 is an enlarged bottom view of the mount of FIG. 16.
Figure 24:
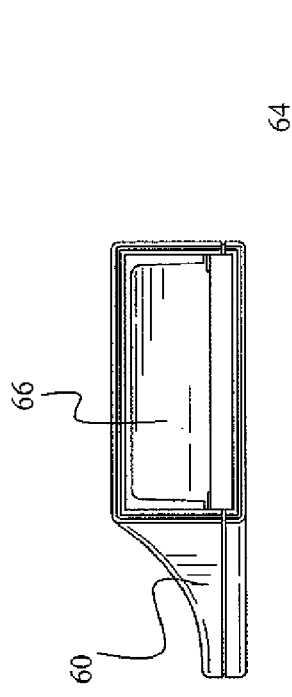
FIG. 24 is an enlarged front view of the collection mouthpiece of FIG. 23.
Figure 25:
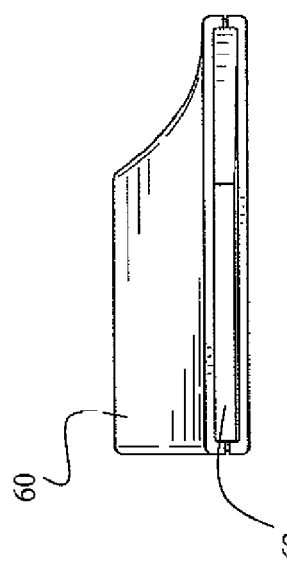
FIG. 25 is an enlarged rear view of the collection mouthpiece of FIG. 23.
Figure 26:
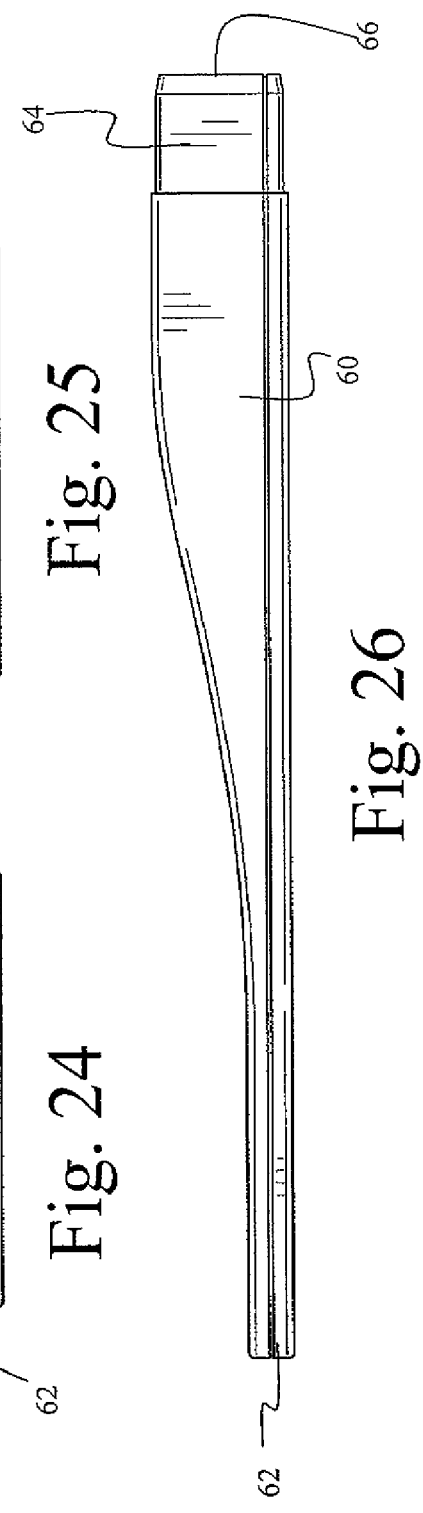
FIG. 26 is an enlarged right side view of the collection mouthpiece of FIG. 23.
Figure 27:
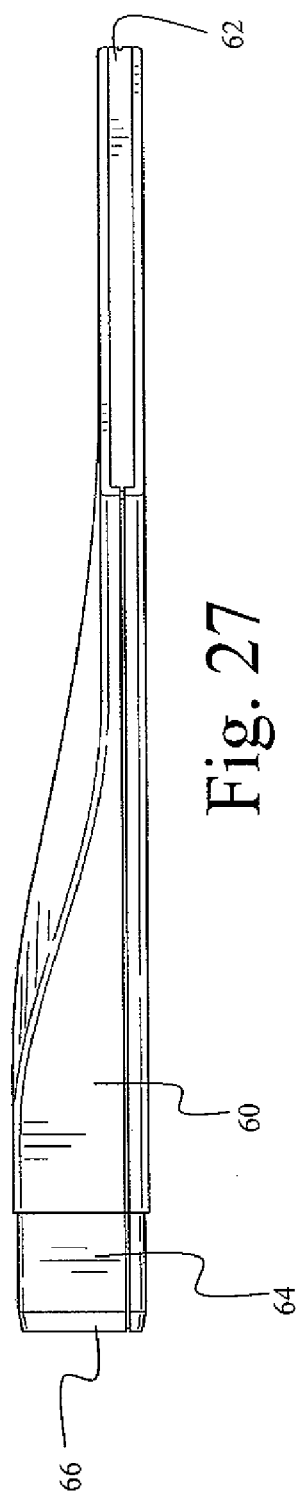
FIG. 27 is an enlarged left side view of the collection mouthpiece of FIG. 23.
Figure 28:
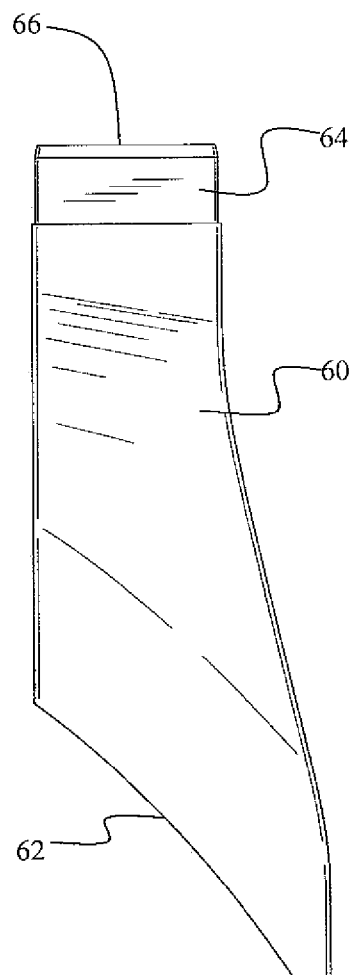
FIG. 28 is an enlarged top view of the collection mouthpiece of FIG. 23.
Figure 29:
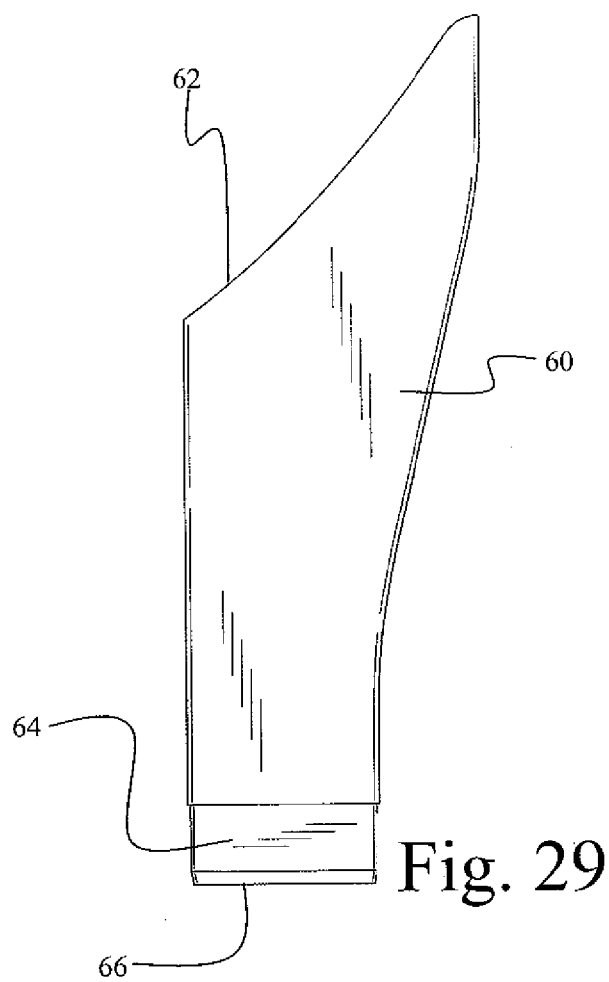
FIG. 29 is an enlarged bottom view of the collection mouthpiece of FIG. 23.
Figure 31:
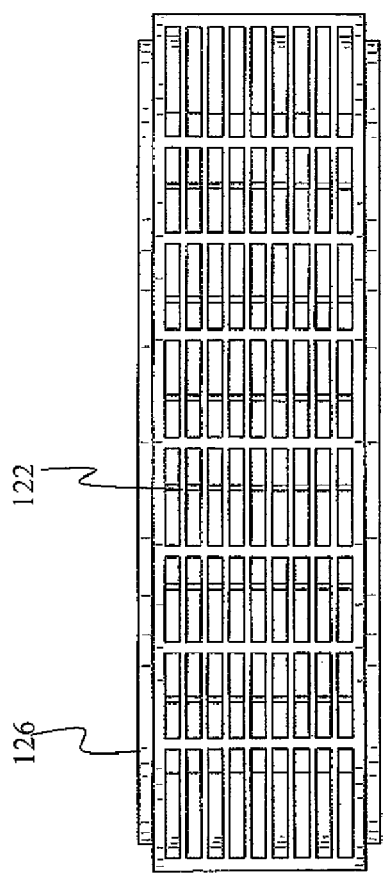
FIG. 31 is an enlarged front view of filter cartridge housing of FIG. 30.
Figure 32:
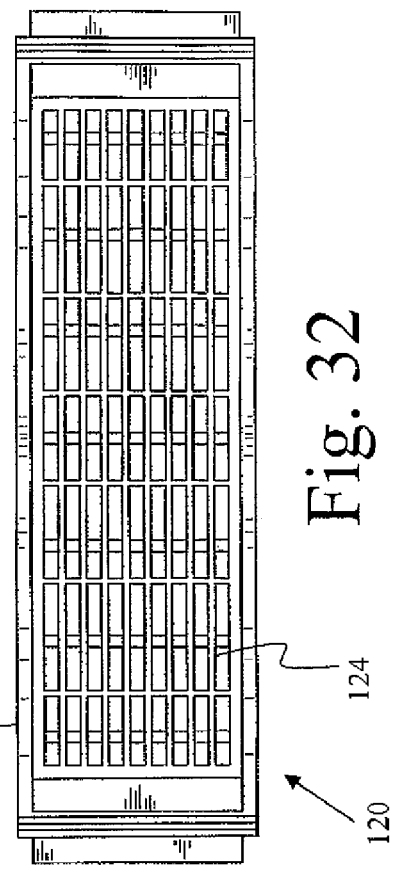
FIG. 32 is an enlarged rear view of the filter cartridge housing of FIG. 30.
Figure 30:
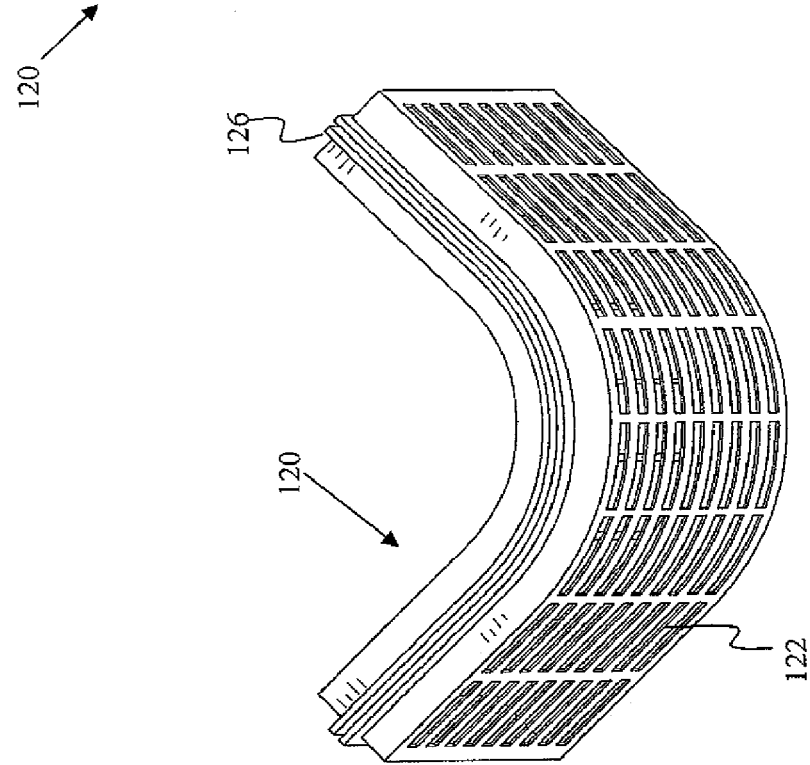
FIG. 30 is an enlarged, upper front perspective view of a filter cartridge housing of the device of FIG. 1.
Figure 33:
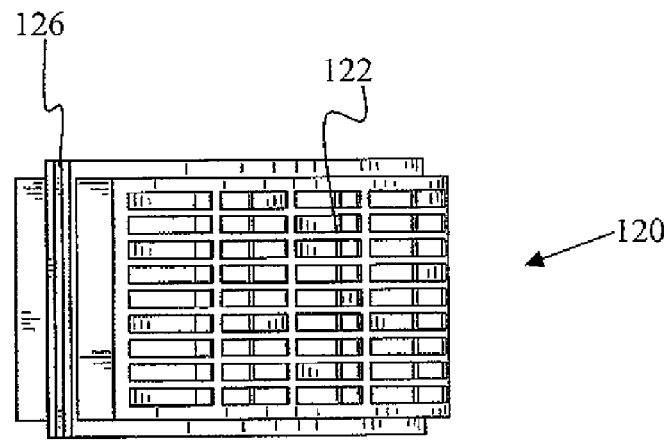
FIG. 33 is an enlarged side view of the filter cartridge housing of FIG. 30.
Figure 34:
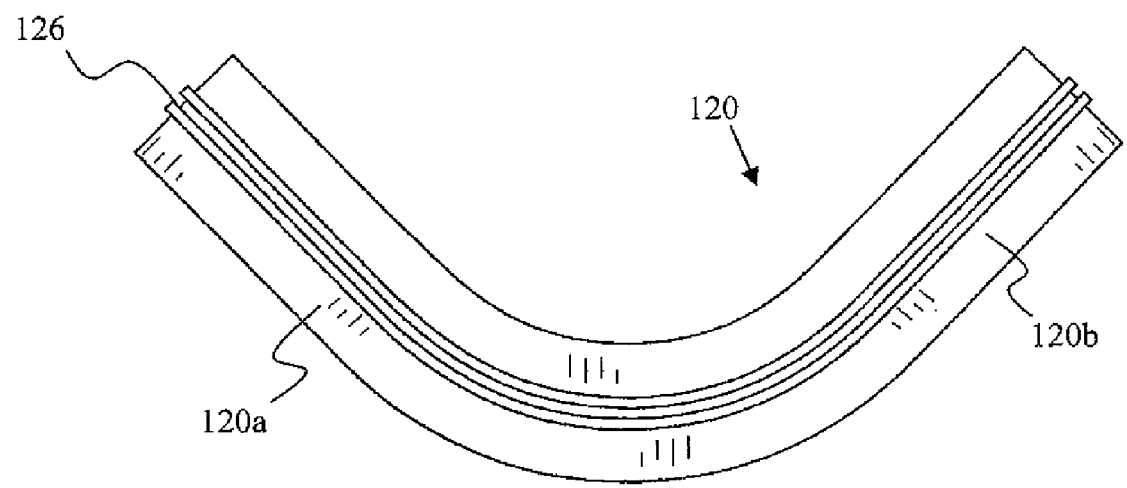
FIG. 34 is an enlarged top view of the filter cartridge housing of FIG. 30, the top view being substantially identical to the bottom view.
Figure 35:
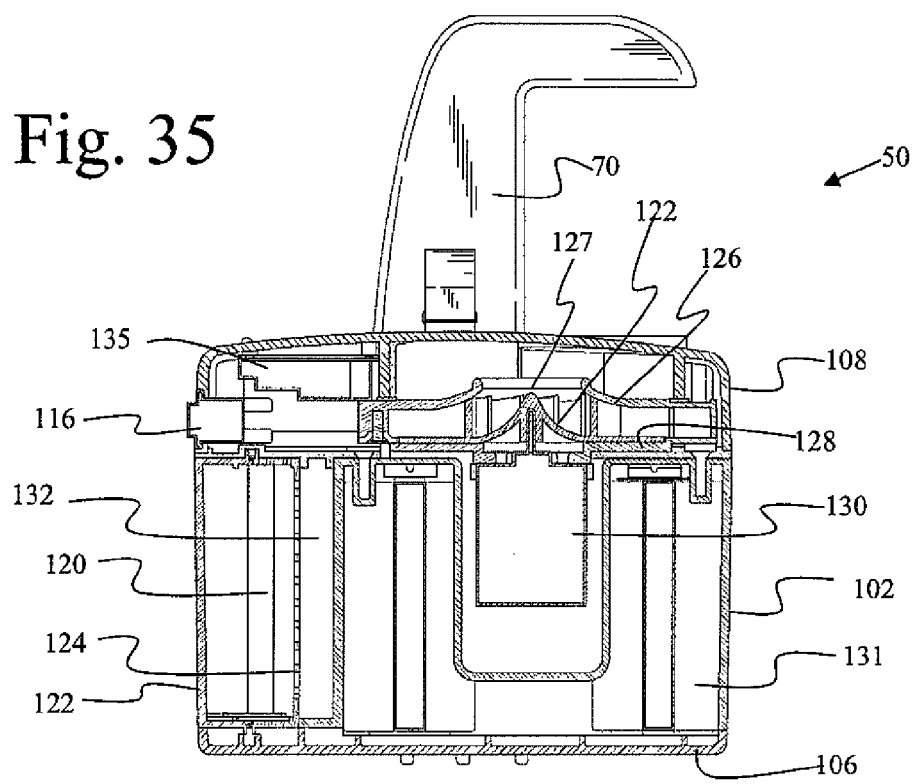
FIG. 35 is a cross-sectional side view of the pump unit taken along line XXXV-XXXV of FIG. 6.
Figure 36:
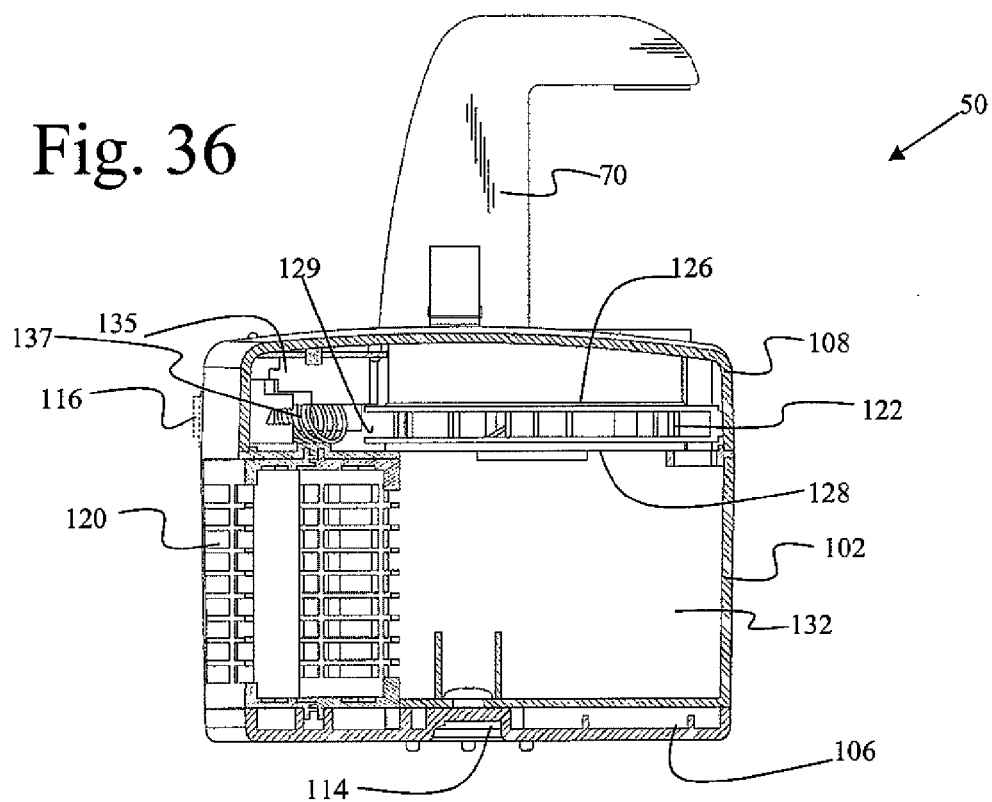
FIG. 36 is a cross-sectional side view of the pump unit taken along line XXXVI-XXXVI of FIG. 6, with filter cartridge housing present.

DETAILED DESCRIPTION OF EXEMPLARY EMBODIMENTS AND EXEMPLARY METHODS OF THE INVENTION

Reference will now be made in detail to exemplary embodiments and methods of the invention as illustrated in the accompanying drawings, in which like reference characters designate like or corresponding parts throughout the drawings. It should be noted, however, that the invention in its broader aspects is not limited to the specific details, representative devices and methods, and illustrative examples shown and described in this section in connection with the exemplary embodiments and methods.

FIGS. 1-9 depict an embodiment of an odor removal (or deodorizing) device, generally designated by reference numeral 50, designed for operation with a standard toilet 200 (FIG. 1). The device 50 is mountable on the toilet 200 without requiring any disassembly, substitution of replacement parts, or permanent modification of the toilet 200 or its components or existing plumbing.

The toilet 200 includes a toilet bowl 202 bolted or otherwise attached to the floor (not shown). The toilet bowl 202 has a discharge passage (not shown) connected to piping (not shown) for communication with a sewage line (not shown). When the toilet 200 is flushed, human waste is removed from the toilet bowl 202 through the discharge passage and sewage line. The toilet bowl 202 has upwardly extending curved walls terminating at an upward facing continuous rim or ledge 204 that surrounds and contains a body of water. The rear region of rim 204 is integral with an apron 206 which extends rearward towards a flush tank or basin 208. Hinges 210 mounted on the rear apron 206 pivotally connect the toilet bowl 202 to an annular toilet seat 212 and a toilet lid or cover 214. The toilet seat 212 and the toilet lid 214 are pivotal about the hinges 210 independently of one another between a raised orientation (for urination) and a lowered orientation (for defecation). Spacers (not shown) known in the art typically protrude from or attached to the bottom surface of the seat 212 to space the bottom surface of the toilet seat 212 apart from the rim 204 when the toilet seat 212 is oriented into its lowered position.

It should be understood that the device 50 may be employed with toilets having various configurations other than illustrated in FIG. 1, as well as toilets having additional or fewer components than those described above. The device 50 may be used, for example, with a toilet not equipped with a flush tank or toilet lid. Further, while the accompanying drawings depict the device 50 mounted on the left side (from the reference point of a seated user) of the toilet 200, the device 50 may be designed to permit mounting and operation from the opposite, right side of the toilet 200 or immediately behind the toilet 200 or elsewhere. The device 50 may be used with "Porta-Potties," that is mobile toilet sheds, marine heads, one-piece molded toilets, etc.

Although illustrated and described primarily with respect to the removal of odors from a toilet 200 or bathroom area, it should be understood that the deodorizing device 50 in its broader aspects has universal deodorizing applications. Alternative intended applications include elimination or reduction of cigarette smoke from residential or office environments, reduction or removal of solvents and lacquer vapor odors from nail technician locations, RV compartment deodorizers, or general open area or closed room odor removal. As will be described in further detail below, operation in these alternative environments may call for substitution or elimination of certain components of the device 50 illustrated in the accompanying figures.

As an overview to the exemplary embodiment illustrated in FIGS. 1-9, the deodorizing device 50 includes a collection mouthpiece 60 for collecting fumes from a toilet bowl 202, a mount 70 in operable communication with the collection mouthpiece 60 to receive the fumes and secure the device 50 to the toilet 200, and a pump/filter housing unit (or pump unit) 100 in operable communication with the mount 70 to draw in and filter the fumes. Each of these components is discussed in greater detail below. It should be understood that the deodorizing device 50 may include additional components or fewer components than shown.

The collection mouthpiece 60 is best seen in the enlarged view of FIGS. 23-29. The collection mouthpiece 60 has a first end with a forward-facing oblong air intake port 62 shaped to fit under the toilet seat 212. The elongated width of the intake port 62 broadens the intake area to permit withdrawal of a relatively high volume of malodorous air and fumes from the narrow area between the toilet seat 212 and the rim 204 of the toilet 200. The intake port 62 is in communication with a continuous channel that extends along the entire length of the collection mouthpiece 60. At the opposite second end of the collection mouthpiece 60, a fitting portion 64 with a channel outlet 66 is provided. The fitting portion 64 has slightly decreased outer dimensions, so that the fitting portion 64 may be inserted into and attached to an inlet port 74 of the mount 70 by friction-fit engagement.

The collection mouthpiece 60 is illustrated as having a taper from its intake port 62 end to its channel outlet 66 end. The forward edge of the collection mouthpiece 60 is generally concave to match the curvature of the outer edge of the rim 204 or the inner edge of the toilet seat 212. It should be understood, however, that the collection mouthpiece 60 may possess other configurations and front edge profiles. The collection mouthpiece 60 may be made of a plastic, such as PVC, or any other material suitable for its intended use. In the event that the collection mouthpiece 60 is intended to be disposable, it desirably may be made of a biodegradable material, and can even be made of wood or other cellulosic material. The collection mouthpiece 60 is illustrated as a monolithic (or unitary) body. It should be understood that the body of the collection mouthpiece 60 may be constituted by two or more pieces permanently or detachably joined together.

When the deodorizing device 50 is mounted (discussed below) for operation on the toilet 200, the collection mouthpiece 60 preferably either rests on or is suspended above the toilet bowl rim 204 and below the toilet seat 212 (when in its lowered position). The collection mouthpiece 60 extends to the side of the hinges 210 and penetrates the space defined between the bottom surface of the toilet seat 212 and the upper surface of the rim 204 without interfering with pivotal movement of the seat 212 between its raised position and its lowered position. The front edge of the collection mouthpiece 60 may be spaced apart rearward from the inner edge of the rim 204 so as to reduce exposure to male urination and simplify cleaning the toilet 200. The spacing between the forward-facing edge of the collection mouthpiece 60 the inner edge of the rim 204 may be, for example, about 2.54 cm (about 1 inch).

One advantage of mounting and positioning the collection mouthpiece 60 to the side of the toilet 200 rather than behind the seat 212 is that the collection mouthpiece 60 does not need to extend over and along the rear apron 206. Adverse aesthetic impact is thereby lessened, and parts and manufacturing costs are reduced. The collection mouthpiece 60 may be made sufficiently small and accessible to permit its affordable production and use as a disposal unit which may be thrown away and replaced after it has been sullied.

The mount 70 is embodied in the drawings as a clamp bracket, but may take other forms. The embodied mount 70, best seen in the enlarged views of FIGS. 16-22, includes a main body 72 having an internal channel continuously extending from an inlet port 74 to an outlet port 76. The inlet port 74 is located at the top of the mount 70 and is sized to receive the fitting portion 64 of the collection mouthpiece 60 in a friction-fit male/female engagement to secure the collection mouthpiece 60 in its operative position, i.e., with the intake port 62 near the edge of the toilet bowl 202. In the illustrated embodiment, the inlet port 74 is the female member, although the design may be adapted to provide the inlet port 74 portion as a male member received by channel outlet 66 of the collection mouthpiece 60. In either event, a communicating relationship is established between the respective channels of the collection mouthpiece 60 and the mount 70. The connection is designed to communicate the inlet port 74 of the mount 70 to the intake port 62 of the collection mouthpiece 60, so that malodorous air and fumes feed into the air intake port 62, through the collection mouthpiece 60, and along the internal channel of the mount 70 to the pump unit 100.

As mentioned above, the mount 70 includes a clamp bracket feature. A first or upper clamp bracket end 78 is spaced apart from an adjustable second or lower clamp bracket end 80. The first clamp bracket end 78 is integrally formed with (that is, monolithic to) the main body 72 of the mount 70 and has a smooth, rounded upper surface. The lower clamp bracket end 80 is positioned at approximately mid-length along the height of the mount 70 and is constituted by a pair of screw-threaded toggles 82 in the form of pivotal arms which independently swivel relative to the main body 72. Each of the toggles 82 includes a threaded hole 83 for receiving a respective wing bolt 84 (FIG. 1). It should be understood that the mount 70 may include one, two, or three or more such toggles 82. The provision of multiple toggles 82 for engagement with the toilet 200 enhances mounting stabilization, preventing or reducing wobbling of the device 50. The wing bolts 84 may be replaced with alternative fasteners. Fasteners that do not require tools for the installation and removal of the mount 70 relative to the toilet 200 are preferred.

To secure the mount 70 (and the remainder of the device 50 connected to the mount 70) to the toilet 200, the first clamp bracket end 78 is placed on the upper surface of the apron 206 of the toilet 200 to establish an overhang, and the second clamp bracket end 80 is positioned (e.g., pivoted) below the lower surface of the toilet rear apron 206. The wing bolts 84 are rotated and driven upward through the vertical threaded holes 83 of the toggles 82 until the upper ends of the wing bolts 84 come into clamping contact with the lower surface of the toilet apron 206. The upper ends of the wing bolts 84 may be provided with pads or bumpers so as not to damage the lower surface of the rear apron 206.

The mount 70 embodied in the accompanying drawings has several advantages. First, the adjustable wing bolts 84 and toggling feature of bracket end 80 allow the mount 70 to be clamped to toilets 200 having various sizes, shapes, and apron thicknesses. Second, the mount 70 is designed to attach to the toilet 200, such as at the rear apron 206 of the toilet 200, so as to suspend the entire device 50 above the floor, thereby leaving the floor accessible for cleaning, mopping and polishing without requiring removal or relocation of the device 50. While the exemplary embodiment is illustrated in a suspended state, it should be understood that one or more components of device 50 may be positioned directly on the floor. Third, the mount 70 substantially hides the device 50 from view by setting it towards the back of the toilet 200 and preferably at least partially under the toilet tank 208. In this concealed position, the bulk of the device 50 is out of sight (from a viewpoint in front of the toilet 200) for enhancing aesthetics and relatively free from exposure to male urination.

As briefly described above, the main body 72 of the mount 70 has an internal channel extending from an inlet port 74 to an outlet port 76. Incorporation of the internal channel into the main body 72 of the mount 70 enhances the aesthetics of the device 50 and simplifies design by eliminating the need for separate hoses and pipes between the collection mouthpiece 60 and the pump unit 100. The outlet port 76 feeds into a suction inlet port 104 of the pump unit 100, as discussed in greater detail below.

To permit attachment of the pump unit 100 to the mount 70, the mount 70 includes a flexible catch 90 with a release tab 92 located immediately above the outlet port 76. The release tab 92 is operatively connected to the catch 90 to permit flexible movement of the catch 90 into and out of engagement with the top of the pump unit 100, as discussed below. At the lower end of the mount 70 a support ledge 94 is provided for supporting the bottom of the pump unit 100, also discussed below. The catch 90 and the support ledge 94 are spaced from one another by a distance approximately equal to the height of the pump unit 100. At the tip of the support ledge 94 are upward-extending locking tongues 96 for engaging a recess 110 in the bottom of the pump unit 100.

The mount 70 may be made of any suitable material, although plastics are currently contemplated as exemplary materials. The wing bolts 84 and bumper or pad (not shown) also may be made of any suitable material, such as stainless steel and rubber, respectively. While the mount 70 is shown secured to the apron 206, the adjustability of the mount 70 makes it highly versatile for attachment to other structures, such as a desk top, table top, shelf, and work bench.

The pump (aspiration) unit 100 is best shown in the enlarged views of FIGS. 9-15 and the cross-sectional views 35-38. In the illustrated embodiment the pump unit 100 is self-contained and includes a main housing 102, a bottom plate 106, a cover (or cap) 108 fitted over the top of the main housing 102, and a filter cartridge housing 120 received by the main housing 102. The main housing 102, bottom plate 106, cover 108, and filter cartridge housing 120 collectively define the external surface of the pump unit 100. The external surface of the pump unit 100 has rounded edges and corners for safety and ease of cleaning. The main housing 102, the bottom plate 106, the cover 108, and the filter cartridge housing 120 may be made of the same material, such as plastic.

The suction inlet port 104 of the cover 108 is sized and positioned to receive the outlet port 76 of the mount 70 in friction-fit engagement to provide a hermetic seal. Friction-fit engagement assists in the quick and easy attachment and detachment of the pump unit 100 to and from the mount 70 without the need for tools, as discussed in greater detail below.

The bottom plate 106 is relatively flat for permitting the pump unit 100 to be stably seated on a flat surface, for example, in the event that the pump unit 100 rests on the floor or on a table rather than being suspended by the mount 70 as shown in FIG. 1. The bottom plate 106 includes the recess 110 for mating with the tongue 96 of the support ledge 94 of the mount 70. The upper external surface of the cover 108 includes one or more grooves 112 for mating with the catch 90 of the mount 70. The recess and grooves 110 and 112 are vertically aligned below and above the suction inlet port 104.

To connect the pump unit 100 to the mount 70, the bottom plate 106 of the pump unit 100 is seated on the support ledge 94, so that the tongue 96 is received in the recess 110. The catch 90 is flexed upward by applying force (e.g., via the user's thumb) to the release tab 92. While the catch 90 is raised, the pump unit 100 is tilted or otherwise moved to position one of the grooves 112 of the cover 108 below the catch 90. The flexing force is removed from the release tab 92 with the pump in place, and the catch 90 is resiliently returned downward to capture one of the grooves 112 and secure the pump unit 100 between the catch 90 and the support ledge 94. The quick-release attributes of the release tab 92 and the catch 90 permits attachment and detachment of the pump unit 100 with respect to the mount 70 without the need for tools. Easy detachment of the pump unit 100 from the mount 70 facilitates pump unit 100 servicing, such as filter changes and battery replacement or renewal, and improves portability, allowing the pump unit 100 to be easily transported and relocated to other toilets or other locations. Advantageously, the pump unit 100 and the collection mouthpiece 60 may be accessed and removed without detaching the mount 70 from the toilet 200.

The bottom plate 106 is equipped with a quick release latch 114 (FIG. 15) to facilitate access to the batteries 133 and the filter cartridge housing 120 without the need for tools. The bottom plate 106 may include hinges 107 (FIG. 15) for swinging the bottom plate 106 downward while retaining its connection to the main housing 102. Although not shown, the cover 108 similarly may include a quick release lock and/or hinges for accessing the interior of the cover 108 and the main housing 102 from above.

Referring now to the cross-sectional views of FIGS. 35-38, fumes are drawn in or aspirated through the suction inlet port 104 (FIG. 10) by an impeller 122 located in an open compartment of the cover 108 of the pump unit 100. The impeller 122 has a plurality of fins, each with a curved upper edge in an exemplary embodiment. The impeller 122 is interposed between an upper impeller housing plate 126 and a lower impeller housing plate 128 that are parallel to one another. The upper housing plate 126 includes a central aperture 127 immediately above the center of the impeller 122 for receiving incoming air. A lateral outlet passage 129 is defined between the upper and lower housing plates 126, 128 for expelling the air to a compression chamber 132.

An electric motor 130 is positioned below the impeller 122 in the main housing 102, and is surrounded by a battery compartment 131 also located in the main housing 102. The electric motor 130 and batteries 133 in the battery compartment 131 constitute the bulk of the weight of the pump unit 102. For stabilization reasons, the electric motor 130 and the battery compartment 131 are positioned in close proximity to the mount 70. A control circuit board 135 is secured in the cover 108 using a coil 137, although other devices and fasteners may be used to retain the control circuit board 135 in place. The control circuit board 135 is electrically connected to the motor 130, the on/off switch 116, and the sensor 117. Advantageously, the electrical components are substantially isolated from the air flow, so that if water should enter in through the suction inlet port 104 or the filter housing cartridge 120, the water is unlikely to come into contact with these electrical components.

The electric motor 130 is controlled by a switch 116. The switch may be of the simple on/off variety, or may include an off mode, an auto-on mode (for activation by the sensor 117), and a manual-on mode. When activated, the electric motor 130 drives the impeller 122 at an effective speed to create a vacuum or aspirating force for drawing air and fumes within the toilet bowl 202 through the intake port 62 of the collection mouthpiece 60 and along the internal channel of the mount 70 to the pump unit 100. The motor 130 may be battery-operated or adapted to be plugged into a common wall socket or hard-wired into a building electrical grid. In the illustrated embodiment, the motor 130 is powered by four D-size batteries 133. It should be understood that various types of fans, impellers, and power sources may be used, as may other blowing and aspirating devices.

Figure 37:
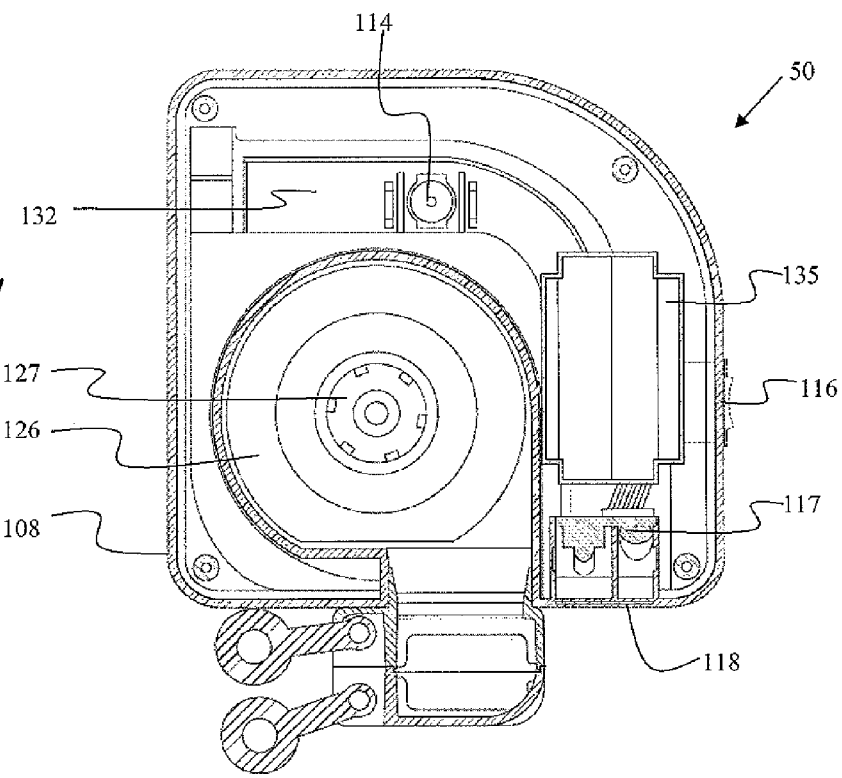
FIG. 37 is a cross-sectional upper view of the pump unit taken along line XXXVII-XXXVII of FIG. 5.
Figure 38:
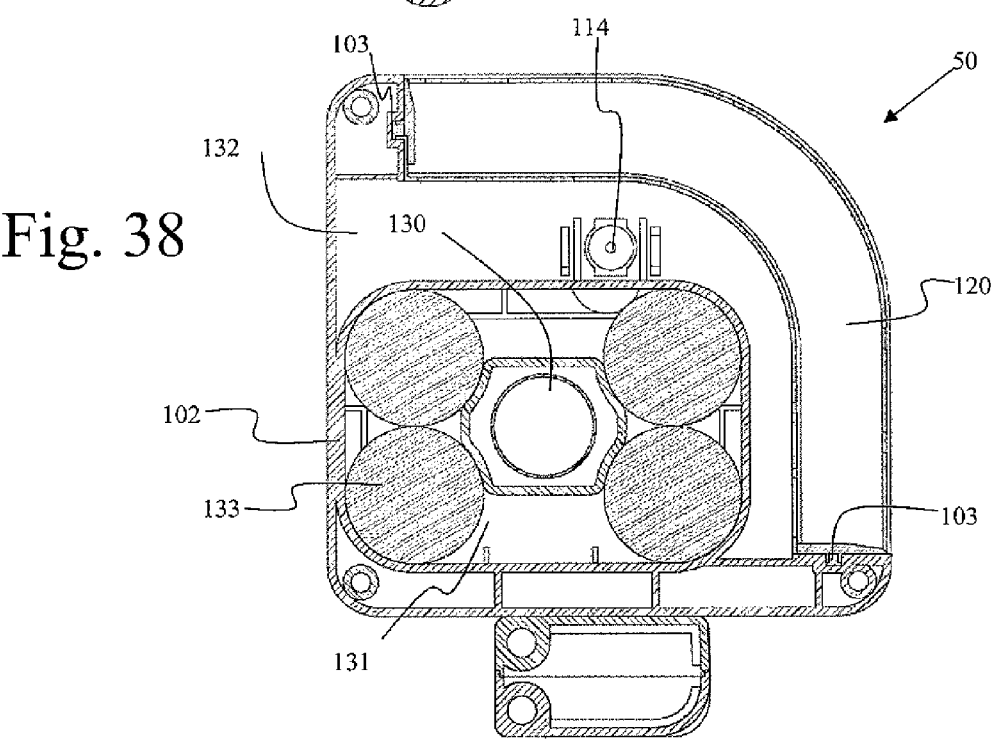
FIG. 38 is a cross-sectional upper view of the pump unit taken along line XXXVIII-XXXVIII of FIG. 5.

The impeller 122 directs the air through the outlet passage 129 defined between the upper and lower housing plates 126, 128 and into the compression chamber 132. As best seen in FIGS. 37 and 38, the compression chamber 132 extends along two sides of the pump unit housing 102. More specifically, the compression chamber 132 is interposed between the battery compartment 131 and the internal surface of the filter cartridge housing 120. The width and height of the compression chamber 132 may be substantially coextensive with the width and height of the filter cartridge housing 120 to ensure that the expelled air/odor is adequately dispersed over substantially all of the interior wall surface area of the filter cartridge housing 120.

The filter cartridge housing 120 generally has an "L" shape composed of first and second wall portions 120a, 120b with a 90 degree curved transition area. The first and second wall portions 120, 120b respectively extend along and define surface portions of two sides—e.g., the right external surface and rear external surface—of the pump unit 100. The first and second wall portions 120a, 120b extend along substantially the entire lengths of the respective sides of the pump unit 100. The dual function of the filter cartridge housing 120 as a filtering member and housing structure assists in compacting the size of the pump unit 100 while providing sufficient filter surface area to eliminate odors.

The filter cartridge housing 120 includes a front grille 122 and a rear grille 124 each having lattice frameworks respectively defining the anterior and posterior surfaces of the filter cartridge housing 120. The lattice structure of the rear grille 124 defines flow openings for introducing air into and through the filter material. Similarly, the lattice structure of the front grille 122 defines flow openings for expelling air from the pump unit 100. The flow openings collectively extend along substantially the entire lengths of two sides—e.g., the right external surface and rear external surface—of the pump unit 100.

An outwardly extending double rib (or tongue) 126 runs continuously around the top, bottom, and opposite ends of the filter cartridge housing 120. The double rib 126 is positioned at the midpoint between the anterior and posterior faces of the filter cartridge housing 120. The rib 126 mates into grooves 103 (shown in FIG. 38) of the main housing 102, the bottom plate 106, and the cover 108. The mating engagement may establish a substantially hermetic seal to force air through the front and rear grills 122, 124 and consequently through the filter material. Although not shown, a sealing or gasket material may be included in the grooves 103.

Removal of the filter cartridge housing 120 is performed by raising the cover 108 or lowering the bottom plate 106 so as to create an opening which exposes the top or bottom edge of the filter cartridge housing 120. The filter cartridge housing 120 is then either raised or lowered through the opening. (In the illustrated embodiment, the bottom plate 106 is lowered by releasing the latch 114 and the housing 120 is lowered through the resulting opening). As the filter cartridge housing 120 is withdrawn, the portions of the rib 126 on the opposite ends of the filter cartridge housing 120 slide along respective grooves 103 of the main housing 102 until the rib 126 completely disengages from the side wall grooves 103. A replacement cartridge may be installed through the opening in the reverse manner to replace the disposed cartridge. The cartridges desirably will be replaced as the filter material within the filter cartridge housing 120 loses its filtering ability.

In an exemplary embodiment, the filter material in the filter cartridge housing 120 is activated carbon. Coconut shell granules have been found to exhibit especially excellent filtering quality, providing adequate deodorizing characteristics in only a single pass. Surprisingly, it has been found that relatively small particle sizes, such as particles having a particle size distribution that can pass through a mesh having a U.S. Sieve Size Number (ASTM) of 12 (e.g., in a range of 12-30 (inclusive)) capable of high compaction is advantageous, as discussed below. It should be understood that other filter materials, such as other carbon materials and zeolites, may be included in the filter cartridge housing 120. The granules may be retained in a nylon mesh material or other permeable material. Additionally or in the alternative, a fragrance source may be contained outside of the filter cartridge housing 120 or elsewhere in the pump unit 100 for adding a pleasant scent. For example, the fragrance may be provided in the form of a scent packet adhered, suspended, or otherwise positioned outside of the filter cartridge housing 120 to intercept treated air.

The high levels of compaction of the filter material created by the use of granules having a particle size distribution that can pass through a mesh having a sieve size number of 12, such as 12-30 sieve size granules, restrict the flow path through the filter cartridge housing 120 to fine interstices between the granules. Consequently, air flow through the filter cartridge housing 120 is slowed, and interaction time between the air and the granules is increased. The continued high-rate influx of air created by the electric motor 130 and restricted egress through the compacted granules combine to build up pressure within the compression chamber 132. As pressure in the chamber 132 is increased, the air is forced through the interstices until escaping through the front grill 122. The forced restricted flow of air over small granules with high surface-to-volume ratios is believed to dramatically increase the deodorizing effect and permit effective odor removal in only a single pass through the filter material. Simultaneously, air intake at the collection mouthpiece 60 is maintained at a high rate to prevent escape of malodorous air from the toilet bowl 202.

It may be desirable for commercial cost savings purposes to use larger and/or less compacted granules in the filter material. However, larger and/or less compacted granules will not have the same effectiveness as smaller, compacted granules in slowing the flow rate of malodorous air passing through the filter material. The faster air flow rate through the larger flow paths between large granules can deleteriously affect filtering effectiveness. To address this potential problem, in a modified embodiment the larger, less compacted granules may be contained in a low permeable containment material. The lower permeability of the containment material of this modified embodiment will slow the flow rate of air passing through the filter cartridge housing 120, thereby providing greater interaction time between the granules and the malodorous air. Because the less permeable material slows the flow rate at the filter cartridge housing 120, pressure will build-up in the compression chamber 132. At the same time, the intake rate of malodorous air by the collection mouthpiece 60 is not sacrificed.

It should be understood that filter cartridge housing 120 may be supplemented with additional ventilation and/or air purification parts and systems. For example, the device 50 may include or be attached to a ventilation system, such as ducts or piping in communication with an exterior vent, e.g., in the ceiling or wall of the bathroom, for expelling filtered air from the room. Generally, however, ventilation systems are not required because of the excellent filtering performance of the device 50.

In an exemplary embodiment the pump unit 100 includes an IR sensor window 118 in the cover 108. An IR sensor 117 behind the window 118 is oriented to permit direct line-of-sight viewing and accurate detecting of the toilet seat 212 area so as to monitor whether a user is seated on the toilet 200. The IR sensor 117 may be equipped with a relatively narrow IR radiation pattern so as to avoid interference from the seat 212 and the lid 214. The sensor 117 may be a photo-reflective type, for example, producing narrow radiation patterns of 4 degrees, with a range of approximately 46 cm (18 inches) so as not to extend beyond about the center of the toilet bowl 202. By limiting the range of the IR beam, the sensor 117 does not detect a person standing (e.g., a male urinating) in front of the toilet 200. The sensor 117 may operate non-continuously, with a microprocessor controlling power to the motor 130. A shutdown delay can be provided during which the pump unit 100 continues to operate after the user leaves the detection area. This shutdown delay, and the resulting continued operation of the pump unit 100, further assists in preventing the escape of odor from the toilet bowl 202 after the user rises from the seat 212, including during a period prior to flushing.

Assembly of the device 50 may be accomplished in several sequences, one of which is detailed below. The mount 70 is positioned for mounting to the apron 206 of the toilet 200 by placing the overhang portion 78 of the mount 70 over the apron 206. The toggles 82 of the mount 70 may be pivoted to positions directly below flat lower surface areas of the apron 206. The wing bolts 84 are rotated and thereby driven upward until their distal ends (or bumpers at their distal ends) are placed in tight engaging contact with the lower surface of the apron 206 to clamp the mount 70 to the apron 206. The fitting portion 64 of the collection mouthpiece 60 is friction fitted into the inlet port 74 of the mount 70. The wing bolts 84 may be slightly loosened to permit the mount 70 to be rotated and maneuvered to locate the intake port 74 of the collection mouthpiece 60 over the toilet rim 204 as described above. After the wing bolts 84 are again tightened into clamping engagement with the apron 206, the pump unit 100 is placed on the support ledge 94 of the mount 70, and tongue 96 is inserted into the recess 110 of the bottom plate 106. The release tab 92 is pushed to flex the catch 90 upward and the pump unit 100 is tilted into position so that the outlet port 76 of the mount 70 is inserted into suction inlet port 104 of the cover 110. The tab 92 is then released to resiliently lower the catch 90 into mating engagement with one of the grooves 112 on the cover 108, securing the pump unit 100 between the catch 90 and the ledge 94 of the mount 70. (It should be understood that the pump unit 100 may be secured to the mount 70 before the mount 70 is clamped to the toilet 200.)

In operation, activation of the on/off switch 116 or an automatic switch controlled by the sensor 117, if present, connects an electric circuit and causes power to be supplied to and drive the motor 130 of the pump unit 100. The motor 130 rotates the impeller 122 at a sufficient speed to draw air from within and proximal to the toilet bowl 202, through the intake port 62 of the collection mouthpiece 60, along the length and out through the outlet port 66 of the collection mouthpiece 60 and into and through the channel of the mount 70. After the air is drawn in through the suction inlet port 104 and directed past the impeller 122, it is fed into the compression chamber 132. The air passes from the compression chamber 132 through the adjacent filter cartridge housing 120 of the pump unit 100, where the air is filtered to remove obnoxious smells. The filtered air is then discharged back into the bathroom or other working environment. In the event that the device 50 includes a ventilation exhaust system, the air is expelled outside through a vent. The device 50 is deactivated by turning the manual on/off switch 116 to the off position or, in the event an automatic switch with sensor 117 is present, by the user rising from the seat 212 of the toilet 200.

One of the main advantages of the odor removal device 50 of the above exemplary embodiment is the simple detachability of the device 50 components, such as the collection mouthpiece 60 and the mount 70 from the toilet 200 and the disassembly of the components from one another without the need for tools, such as screw drivers or wrenches. Cleaning of the odor removal device 50 and the toilet 200, including the area about the rim 204 and the rear apron 206, is thereby facilitated. Another advantage of the deodorizing device 50 of the exemplary embodiment is the ability to retrofit the device 50 inconspicuously on existing toilets without requiring the removal, replacement, or modification of existing toilet hardware or modification to existing plumbing. Other advantages of the odor removal device 50 of the exemplary embodiment include its portability, low cost of manufacture, and simplicity of assembly, and retrofitability to a previously installed toilet 200. It should be understood that the invention may encompass embodiments in which none or fewer than all of these specific advantages are attained.

Figure 39:
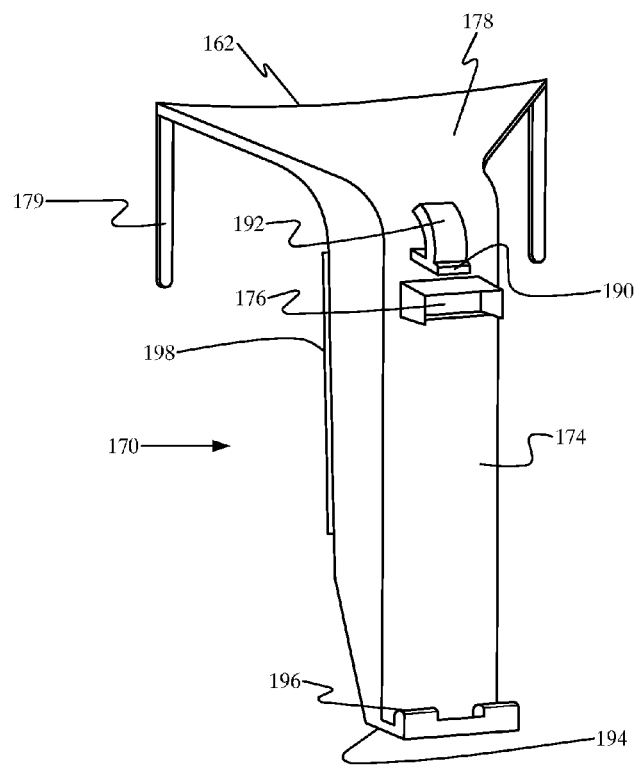
FIG. 39 is a perspective view of an alternative consolidated mount and collection mouthpiece.

It further should be understood that various modifications, alterations, and other changes to the exemplary embodiment are contemplated and fall within the scope of the invention. For example, FIG. 39 is a perspective view of an alternative embodiment especially useful for "Porta-Potty" applications in which a mount 170 is monolithically formed with a collection mouthpiece. (It should be understood that a multi-component collection mouthpiece/mount such as shown in FIG. 1 may be used in Porta-Potty applications.) The mount 170 includes an overhang structure 178 that reaches over the rim 212 of the toilet 200. The overhang structure 178 includes rim hooks 179 that extend partly down the interior of the toilet bowl 202 for securing the mount 170 to the toilet 200. The overhang structure 178 serves the additional function of a collection mouthpiece, characterized by a curved inlet face with an air intake port at 162. An optional foam or sticky pad 198 is positioned on the main body 174 of the mount 170 so as to rest and optionally adhere to the toilet bowl 202 or other part of the toilet 200. The mount 170 further includes an outlet port 176, a catch 190, a release tab 192, a support ledge 194, and a tongue 196 that are constructed and operate substantially the same as their counterparts 74, 90, 92, 94, and 96 of the above-described embodiment so as to make the mounts 70 and 170 interchangeable with one another.

Figure 40:
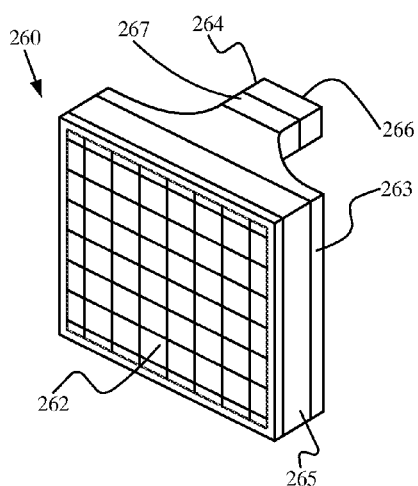
FIG. 40 is a perspective view of an alternative collection mouthpiece.
Figure 41:
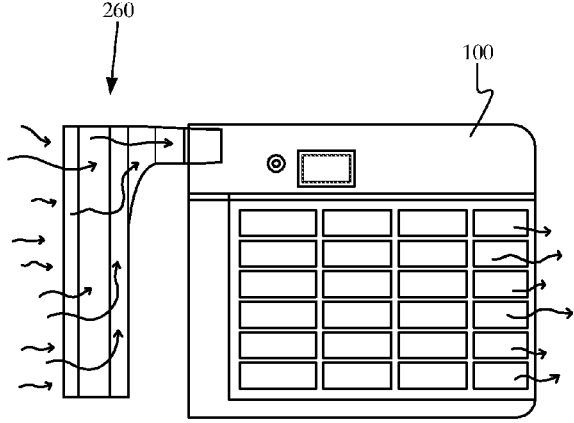
FIG. 41 is a side view of the alternative collection mouthpiece of FIG. 40 connected to the pump unit of FIG. 9.

Another modification involves the elimination of the mount 70, particularly for applications in which the pump unit 100 is seated on a surface, for example, in the case of a "universal" or "desktop" odor eliminator. An example of such an alternative embodiment is shown in FIGS. 40 and 41. The collection mouthpiece 260 includes an intake face 262 having a lattice structure, an outlet side 263, a main body portion 265 sandwiched therebetween, and a fitting portion 264 with a channel outlet 266. The main body portion 265 optionally may include a filter material, which may be the same as or different from the filter material in the filter cartridge housing 120. The fitting portion 264 is inserted directly into the suction inlet port 104 of the pump 100. The collection mouthpiece 260 may be interchangeable with the collection mouthpiece 60 and mount 70 of the first exemplary embodiment. In this regard, the fitting portion 264 may be identical in shape and size to the fitting portion of the mount 70 for fitting engagement with the suction inlet port 104 for increasing the versatility of the device 50. Direct attachment of the mouthpiece 260 to the pump unit 100 allows directional flow of foul air directly into the pump unit 100. Although not shown, an intermediate section 267 between the outlet side 263 and the fitting portion 264 may articulate to improve orientation adjustability of the intake face 262 relative to the suction inlet port 104.

The following specifications represent an exemplary implementation of the deodorizing device 50 for capturing malodorous air and forcing the air through the filter material in the filter cartridge housing 120 in an effective single pass for removing discernible odor. It should be understood that the following specifications are provided as examples, and that specifications outside of the ranges below may be practiced and may be more desirable depending upon the intended application and the size of the area to be deodorized. Further, operation may involve any combination of the following and other specifications.

Collection mouthpiece 20: The intake port 22 of the collection mouthpiece 20 may have an area of, for example, about 2.4 cm (about 0.375 square inch) or greater, such as in a range of about 2.4 cm$^2$ (about 0.375 square inch) to about 4 cm$^2$ (about 0.625 square inch), for example about 3.6 cm$^2$ (about 0.5625 square inch). (For example, an opening with a width of about 7.62 cm (about 3 inches) and a high of about 0.32 cm (about 0.125 inch).) The channel outlet 26 may be, for example, about 4.5 cm$^2$ (about 0.70 square inch) or greater. The intake velocity at the mouthpiece may be in a range of about 8 miles per hour (mph) to about 15 mph, for example 13 mph. The intake volume is preferably in a range of about 0.10 m$^3$/minute (about 4 cubic feet per minute (cfm)) to about 0.20 m$^3$/minute (about 6 cfm).

Mount: The opening areas of the inlet port 34 and outlet port 36 of the mount 30 may be about 4.5 cm$^2$ (about 0.70 square inch) or greater and about 3.2 cm$^2$ (about 0.49 square inch) are greater, respectively.

Motor: The motor may be a DC battery-powered, e.g., four "D"-size batteries 133, or may include an AC adapter for plugging into wall outlets. The motor may have the following specifications:

Variable Operating Range: about 3 to about 9 volts DC
Optimal Voltage Range: about 4.5 to about 6 volts DC
Current Amps (low): about 1.50 to about 1.71 amps
Motor Torque: about 7.00 mN-m (about 71.3 g-cm) or greater
Impeller RPM Range: about 5,800 to about 9,800 rpm.

Impeller: In this exemplary implementation the impeller 122 has a diameter of about 6.67 cm (about 2.625 inches), an outer-edge fin height of about 0.53 cm (about 0.21 inch), and an inner-edge fin height of about 0.89 cm (about 0.35 inch). Air/odor is aspirated through the entrance port 104, about 2.54 cm (about 1 inch) in width.

Filter Specifications: The outer filter surface area may be about 110 cm$^2$ (about 17.0 square inches) or greater, preferably about 129 cm$^2$ (about 20.0 square inches) or greater, and the inner filter surface area may be on the order of about 103 cm$^2$ (about 16 square inches). The total thickness of the filter may be, for example, about 2.22 cm (about 0.875 inches). The volume of activated carbon may be, for example, about 246 cm$^3$ (about 15 cubic inches) or greater. The filter media/carrier may be nylon mesh material, carbon, or media that does not absorb or retain odors or significantly restrict flow. An exemplary filtering material is acid-washed, coconut-based, activated carbon granules having particle size distributions that can pass through a mesh having a United States sieve size number (ASTM) of about 12 (corresponding to mesh size openings of 1.7 mm). That is, the particle sizes are less than the 1.7 mm openings of the No. 12 mesh. In particularly exemplary embodiments, the carbon granules have a particle size distribution corresponding to sieve size numbers in a range of about 12 to about 30 (corresponding to mesh size openings of 0.6 mm). Granules having sieve sizes in a range of 12 to 30 will pass through the 1.7 mm openings of the No. 12 mesh but will not pass through the 0.6 mm openings of the No. 30 mesh.) The activated carbon granules may be compacted as described above. Sufficient compaction may be characterized by the absence of perceivable (to the naked eye) movement of the compacted granules when the filter is shaken.

Internal Compression Chamber: The chamber 132 may have a surface area of, for example, at least about 103 cm$^2$ (about 16 square inches), and in normal operation experience an internal operating gauge pressure (that is, above atmospheric) greater than 0.01 atm (about 0.20 psig), such as between about 0.01 atm (about 0.20 psig) and about 0.05 atm (about 0.80 psig) or higher. The depth of the chamber 132, as measured perpendicularly away from the internal face of the filter, may be about 0.635 cm (about 0.25 inch) or greater (e.g., about 1.27 cm (about 0.5 inches)) to prevent tunneling. The dispersion of the air/odor from the impeller housing outlet into the internal chamber 132 slows the flow velocity and helps assure flow of the air/odor through the filter in a uniform, regulated manner, preventing or at least substantially reducing the tunneling of air/odor through a concentrated area of the filter proximate to the impeller housing outlet.

Sensor: The sensor may operate non-continuously, for example, at a 5.0 second emitter rate to conserve batteries and a 46 cm (18 inch) to 71 cm (28 inch) detection range to avoid false detections. A low battery light may be set at 4.3 volts. A shutdown delay (e.g., 15 seconds) can be provided during which the pump unit 100 continues to operate after the user leaves the detection area.

The foregoing detailed description of the certain exemplary embodiments of the invention has been provided for the purpose of explaining the principles of the invention and its practical application, thereby enabling others skilled in the art to understand the invention for various embodiments and with various modifications as are suited to the particular use contemplated. This description is not intended to be exhaustive or to limit the invention to the precise exemplary embodiments disclosed.

What is claimed is:

1. A deodorizing device, comprising:
   a collection mouthpiece having an intake port and an internal channel; and
   a pump unit attachable to the collection mouthpiece and operable to draw malodorous air into the intake port and through the internal channel when the collection mouthpiece is attached to the pump unit, the pump unit comprising a replaceable filter cartridge and an internal compression chamber for receiving the malodorous air, the filter cartridge including a housing and a filter material contained in the housing for treating the malodorous air, the filter cartridge housing comprising first and second wall portions angled relative to one another and extending along respective sides of the pump unit, the first and second wall portions respectively having first and second exterior surface regions with flow openings for expelling the treated air from the pump unit and further respectively having first and second internal surface regions adjacent to the internal compression chamber for receiving the malodorous air for treatment.

2. The deodorizing device of claim 1, further comprising a mount having a first end attachable to the collection mouthpiece and a second end attachable to the pump unit, the mount having an internal channel that communicates with the collection mouthpiece internal channel when the mount is attached to the collection mouthpiece.

3. The deodorizing device of claim 2, wherein the mount and the collection mouthpiece collectively constitute a monolithic structure.

4. The deodorizing device of claim 2, wherein the mount and the collection mouthpiece each contain a fitting portion sized to be interchangeably friction fitted with a suction inlet port of the pump unit.

5. The deodorizing device of claim 2, wherein the mount comprises a bracket clamp.

6. The deodorizing device of claim 5, wherein the mount is adapted to suspend the pump unit from a toilet bowl, and wherein the intake port of the collection mouthpiece is sized to fit in a standard space between a toilet seat and a toilet bowl rim.

7. The deodorizing device of claim 5, wherein the mount is toollessly attachable and detachable from the pump unit.

8. The deodorizing device of claim 1, wherein the flow openings of the first and second wall portions collectively extend along substantially the entire lengths of the respective sides of the pump unit.

9. The deodorizing device of claim 8, wherein the first and second wall portions are angled about 90 degrees relative to one another.

10. The deodorizing device of claim 1, wherein the filter material comprises activated carbon granules having a particle size distribution that passes through a mesh having a U.S. sieve size number of 12.

11. The deodorizing device of claim 10, wherein the activated carbon granules comprise coconut shell.

12. A deodorizing device, comprising:
a collection mouthpiece having an intake port and an internal channel;
a pump unit attachable to the collection mouthpiece and operable to draw malodorous air into the intake port and through the internal channel when the collection mouthpiece is attached to the pump unit, the pump unit comprising a replaceable filter cartridge and an internal compression chamber for receiving the malodorous air, the filter cartridge including a housing and a filter material contained in the housing for treating the malodorous air, the filter cartridge housing comprising first and second wall portions angled relative to one another and extending along respective sides of the pump unit, the first and second wall portions respectively having first and second exterior surface regions with flow openings for expelling the treated air from the pump unit and further respectively having first and second internal surface regions adjacent to the internal compression chamber for receiving the malodorous air for treatment;
an electric motor;
an impeller operably connected to the electric motor; and
an impeller housing that houses the impeller, the impeller housing having an outlet opening for feeding the malodorous air to the compression chamber.

13. The deodorizing device of claim 12, wherein the flow openings of the first and second wall portions collectively extend along substantially the entire lengths of the respective sides of the pump unit.

14. The deodorizing device of claim 13, wherein the first and second wall portions are angled about 90 degrees relative to one another.

15. A deodorizing device, comprising:
a pump unit operable to draw malodorous air into the intake port and through an internal channel of the pump unit, the pump unit comprising a filter cartridge and an internal chamber for receiving the malodorous air, the filter cartridge including a housing and a filter material contained in the housing for treating the malodorous air, the filter cartridge housing comprising first and second wall portions angled relative to one another and extending along respective sides of the pump unit, the first and second wall portions respectively having first and second exterior surface regions with flow openings for expelling the treated air from the pump unit, the first and second exterior surface regions defining first and second outer surfaces of the pump unit.

16. The deodorizing device of claim 15, wherein the first and second wall portions further respectively have first and second internal surface regions adjacent to the internal chamber for receiving the malodorous air for treatment.

17. The deodorizing device of claim 15, further comprising:
an electric motor;
an impeller operably connected to the electric motor; and
an impeller housing that houses the impeller, the impeller housing having an outlet opening for feeding the malodorous air to the internal chamber.

18. The deodorizing device of claim 15, wherein the flow openings of the first and second wall portions collectively extend along substantially the entire lengths of the respective sides of the pump unit.

19. The deodorizing device of claim 15, wherein the first and second wall portions are angled about 90 degrees relative to one another.

20. The deodorizing device of claim 15, further comprising:
a collection mouthpiece attachable to the intake port of the pump unit.

* * * * *